US012758382B2

(12) United States Patent
Rafiee et al.

(10) Patent No.: US 12,758,382 B2
(45) **Date of Patent: *Oct. 13, 2026**

(54) DEVICES, SYSTEMS AND METHODS FOR REPAIRING LUMENAL SYSTEMS

(71) Applicant: Transmural Systems LLC, Andover, MA (US)

(72) Inventors: Nasser Rafiee, Andover, MA (US); G. Randall Green, Skaneateles, NY (US); Adam Groothuis, Swampscott, MA (US)

(73) Assignee: Transmural Systems, LLC, Andover, MA (US)

(*) Notice: Subject to any disclaimer, the term of this patent is extended or adjusted under 35 U.S.C. 154(b) by 95 days.

This patent is subject to a terminal disclaimer.

(21) Appl. No.: 18/655,063

(22) Filed: May 3, 2024

(65) Prior Publication Data

US 2024/0285405 A1 Aug. 29, 2024

Related U.S. Application Data

(63) Continuation of application No. 17/086,106, filed on Oct. 30, 2020, now Pat. No. 12,053,378, which is a (Continued)

(51) Int. Cl.

*A61F 2/24* (2006.01)
*A61B 17/04* (2006.01)

(Continued)

(52) U.S. Cl.

CPC ........ *A61F 2/2436* (2013.01); *A61B 17/0401* (2013.01); *A61F 2/2409* (2013.01);

(Continued)

(58) Field of Classification Search

CPC .......... A61F 2/24; A61F 2/243; A61F 2/2409; A61F 2/2412; A61F 2/2418;

(Continued)

(56) References Cited

U.S. PATENT DOCUMENTS

| | | | |
|---|---|---|---|
| 4,106,129 | A | 8/1978 | Carpentier et al. |
| 4,218,783 | A | 8/1980 | Reul |

(Continued)

FOREIGN PATENT DOCUMENTS

| | | | |
|---|---|---|---|
| EP | 2412397 | A1 | 2/2012 |
| RU | 100718 | U1 | 12/2010 |

(Continued)

OTHER PUBLICATIONS

Final Office Action with notification date of Jul. 19, 2022, in related U.S. Appl. No. 16/400,020, 13 pages.

(Continued)

*Primary Examiner* — Tuan V Nguyen

(74) *Attorney, Agent, or Firm* — DeWitt LLP; Brian R. Pollack, Esq.

(57) ABSTRACT

The disclosure provides valve prostheses and methods of installation. One embodiment of the prosthesis has a generally tubular body adapted for placement proximate a mitral annulus. The tubular body has a generally tubular upper portion adapted to substantially reside in the left atrium above the mitral annulus. The generally tubular upper portion has a first circumferential wall that is outwardly biased to urge against cardiac tissue of the left atrium. The tubular body also includes a lower portion extending downwardly from the generally tubular upper portion, the lower portion being configured to substantially reside in the left ventricle below the mitral annulus. The lower portion of this embodiment can be defined by an generally circumferential wall that extends downwardly from the generally tubular upper portion. The generally circumferential wall has a first circumferential end and a second circumferential end, and defines a circumferential extent therebetween.

21 Claims, 22 Drawing Sheets

Related U.S. Application Data continuation-in-part of application No. 16/557,171, filed on Aug. 30, 2019, now Pat. No. 11,357,627, and a continuation-in-part of application No. 16/400,020, filed on Apr. 30, 2019, now Pat. No. 11,839,543, said application No. 16/557,171 is a continuation of application No. 15/413,017, filed on Jan. 23, 2017, now Pat. No. 10,398,551, said application No. 16/400,020 is a continuation of application No. 14/453,478, filed on Aug. 6, 2014, now Pat. No. 10,449,046, which is a continuation of application No. PCT/US2014/049629, filed on Aug. 4, 2014, said application No. 15/413,017 is a continuation-in-part of application No. 14/074,517, filed on Nov. 7, 2013, now Pat. No. 9,549,817.

(60) Provisional application No. 62/007,369, filed on Jun. 3, 2014, provisional application No. 61/878,264, filed on Sep. 16, 2013, provisional application No. 61/862,041, filed on Aug. 4, 2013, provisional application No. 61/723,734, filed on Nov. 7, 2012.

(51) Int. Cl.
*A61B 17/22* (2006.01)
*A61B 17/064* (2006.01)

(52) U.S. Cl.
CPC .......... *A61F 2/2418* (2013.01); *A61F 2/2454* (2013.01); *A61F 2/2457* (2013.01); *A61B 2017/0409* (2013.01); *A61B 2017/0441* (2013.01); *A61B 2017/0649* (2013.01); *A61B 2017/22068* (2013.01); *A61F 2220/0008* (2013.01); *A61F 2250/0003* (2013.01)

(58) Field of Classification Search
CPC .... A61F 2/2427; A61F 2/2436; A61F 2/2454; A61F 2/2457; A61B 17/0401; A61B 17/12009
See application file for complete search history.

(56) References Cited

U.S. PATENT DOCUMENTS

| | | | |
|---|---|---|---|
| 4,259,753 | A | 4/1981 | Liotta et al. |
| 4,666,442 | A | 5/1987 | Arru et al. |
| 4,692,164 | A | 9/1987 | Dzemeshkevich et al. |
| 5,411,552 | A | 5/1995 | Andersen et al. |
| 5,449,384 | A | 9/1995 | Johnson |
| 5,606,928 | A | 3/1997 | Religa et al. |
| 5,788,715 | A | 8/1998 | Watson, Jr. et al. |
| 5,843,167 | A | 12/1998 | Dwyer |
| 5,861,028 | A | 1/1999 | Angell |
| 5,895,410 | A | 4/1999 | Forber et al. |
| 5,928,281 | A | 7/1999 | Huynh et al. |
| 6,059,769 | A | 5/2000 | Lunn et al. |
| 6,106,510 | A | 8/2000 | Lunn et al. |
| 6,375,774 | B1 | 4/2002 | Lunn et al. |
| 6,419,695 | B1 | 7/2002 | Gabbay |
| 6,599,303 | B1 | 7/2003 | Peterson |
| 6,602,271 | B2 | 8/2003 | Adams et al. |
| 6,716,231 | B1 | 4/2004 | Rafiee et al. |
| 6,733,525 | B2 | 5/2004 | Yang et al. |
| 6,790,229 | B1 | 9/2004 | Berreklouw |
| 6,797,000 | B2 | 9/2004 | Simpson et al. |
| 6,800,081 | B2 | 10/2004 | Parodi |
| 6,866,677 | B2 | 3/2005 | Douk et al. |
| 6,869,444 | B2 | 3/2005 | Gabbay |
| 6,893,459 | B1 | 5/2005 | Macoviak |
| 6,911,036 | B2 | 6/2005 | Douk et al. |
| 6,953,476 | B1 | 10/2005 | Shalev |
| 6,960,217 | B2 | 11/2005 | Bolduc |
| 7,044,958 | B2 | 5/2006 | Douk et al. |
| 7,066,946 | B2 | 6/2006 | Douk et al. |
| 7,189,259 | B2 | 3/2007 | Simionescu et al. |
| 7,195,641 | B2 | 3/2007 | Palmaz et al. |
| 7,201,772 | B2 | 4/2007 | Schwammenthal et al. |
| 7,294,135 | B2 | 11/2007 | Stephens et al. |
| 7,316,706 | B2 | 1/2008 | Bloom et al. |
| 7,399,315 | B2 | 7/2008 | Iobbi |
| 7,425,219 | B2 | 9/2008 | Quadri |
| 7,442,204 | B2 | 10/2008 | Schwammenthal et al. |
| 7,442,207 | B2 | 10/2008 | Rafiee |
| 7,445,631 | B2 | 11/2008 | Salahieh et al. |
| 7,481,838 | B2 | 1/2009 | Carpentier et al. |
| 7,491,232 | B2 | 2/2009 | Bolduc et al. |
| 7,524,330 | B2 | 4/2009 | Berreklouw |
| 7,655,040 | B2 | 2/2010 | Douk et al. |
| 7,682,352 | B2 | 3/2010 | Rafiee et al. |
| 7,699,892 | B2 | 4/2010 | Rafiee et al. |
| 7,716,801 | B2 | 5/2010 | Douk et al. |
| 7,753,840 | B2 | 7/2010 | Simionescu et al. |
| 7,753,949 | B2 | 7/2010 | Lamphere et al. |
| 7,780,726 | B2 | 8/2010 | Seguin |
| 7,799,069 | B2 | 9/2010 | Bailey et al. |
| 7,806,917 | B2 | 10/2010 | Xiao |
| 7,806,919 | B2 | 10/2010 | Bloom et al. |
| 7,815,673 | B2 | 10/2010 | Bloom et al. |
| 7,947,072 | B2 | 5/2011 | Yang et al. |
| 7,955,384 | B2 | 6/2011 | Rafiee et al. |
| 7,972,370 | B2 | 7/2011 | Douk et al. |
| 7,998,188 | B2 | 8/2011 | Zilla et al. |
| 8,002,825 | B2 | 8/2011 | Letac et al. |
| 8,052,750 | B2 | 11/2011 | Tuval et al. |
| 8,062,355 | B2 | 11/2011 | Figulla et al. |
| 8,070,802 | B2 | 12/2011 | Lamphere et al. |
| 8,092,518 | B2 | 1/2012 | Schreck |
| 8,092,520 | B2 | 1/2012 | Quadri |
| 8,092,524 | B2 | 1/2012 | Nugent et al. |
| 8,226,710 | B2 | 7/2012 | Nguyen et al. |
| 8,252,051 | B2 | 8/2012 | Chau et al. |
| 8,308,798 | B2 | 11/2012 | Pintor et al. |
| 8,337,541 | B2 | 12/2012 | Quadri et al. |
| 8,348,995 | B2 | 1/2013 | Tuval et al. |
| 8,348,996 | B2 | 1/2013 | Tuval et al. |
| 8,353,954 | B2 | 1/2013 | Cai et al. |
| 8,353,955 | B2 | 1/2013 | Styrc et al. |
| 2001/0021872 | A1 | 9/2001 | Bailey et al. |
| 2002/0032481 | A1 | 3/2002 | Gabbay |
| 2002/0138138 | A1 | 9/2002 | Yang |
| 2003/0055495 | A1 | 3/2003 | Pease et al. |
| 2003/0065386 | A1 | 4/2003 | Weadock |
| 2003/0097172 | A1 | 5/2003 | Shalev et al. |
| 2003/0199975 | A1* | 10/2003 | Gabbay ................ A61F 2/2454 623/1.14 |
| 2004/0087998 | A1 | 5/2004 | Lee et al. |
| 2004/0127916 | A1 | 7/2004 | Bolduc et al. |
| 2004/0260317 | A1 | 12/2004 | Bloom et al. |
| 2005/0038508 | A1 | 2/2005 | Gabbay |
| 2005/0038509 | A1 | 2/2005 | Ashe |
| 2005/0043790 | A1 | 2/2005 | Seguin |
| 2005/0055082 | A1 | 3/2005 | Ben-Muvhar et al. |
| 2005/0137769 | A1 | 6/2005 | Salahieh et al. |
| 2005/0143809 | A1 | 6/2005 | Salahieh et al. |
| 2005/0177180 | A1 | 8/2005 | Kaganov et al. |
| 2005/0288706 | A1 | 12/2005 | Widomski et al. |
| 2006/0085012 | A1 | 4/2006 | Dolan |
| 2006/0106449 | A1 | 5/2006 | Ben-Muvhar |
| 2006/0106450 | A1 | 5/2006 | Ben-Muvhar |
| 2006/0173537 | A1 | 8/2006 | Yang et al. |
| 2006/0259135 | A1 | 11/2006 | Navia et al. |
| 2007/0016288 | A1 | 1/2007 | Gurskis |
| 2007/0043435 | A1 | 2/2007 | Seguin et al. |
| 2007/0067029 | A1 | 3/2007 | Gabbay |
| 2007/0250160 | A1 | 10/2007 | Rafiee |
| 2007/0255398 | A1 | 11/2007 | Yang et al. |
| 2007/0260305 | A1 | 11/2007 | Drews et al. |
| 2007/0288089 | A1 | 12/2007 | Gurskis et al. |
| 2007/0293942 | A1 | 12/2007 | Mizraee |
| 2008/0021537 | A1 | 1/2008 | Ben-Muvhar et al. |
| 2008/0065191 | A1 | 3/2008 | Bolduc et al. |
| 2008/0071369 | A1 | 3/2008 | Tuval |

(56) References Cited

U.S. PATENT DOCUMENTS

| | | | |
|---|---|---|---|
| 2008/0077234 | A1 | 3/2008 | Styrc |
| 2008/0125860 | A1 | 5/2008 | Webler et al. |
| 2008/0208328 | A1 | 8/2008 | Antocci et al. |
| 2008/0221672 | A1 | 9/2008 | Lamphere et al. |
| 2008/0281411 | A1 | 11/2008 | Berreklouw |
| 2009/0005863 | A1 | 1/2009 | Goetz et al. |
| 2009/0062841 | A1 | 3/2009 | Amplatz et al. |
| 2009/0149949 | A1 | 6/2009 | Quinn |
| 2009/0270966 | A1 | 10/2009 | Douk et al. |
| 2009/0270976 | A1 | 10/2009 | Douk et al. |
| 2009/0306768 | A1 | 12/2009 | Quadri |
| 2009/0319038 | A1 | 12/2009 | Gurskis et al. |
| 2010/0036479 | A1 | 2/2010 | Hill et al. |
| 2010/0082094 | A1 | 4/2010 | Quadri et al. |
| 2010/0100167 | A1 | 4/2010 | Bortlein et al. |
| 2010/0174363 | A1 | 7/2010 | Castro |
| 2010/0179648 | A1 | 7/2010 | Richter et al. |
| 2010/0179649 | A1 | 7/2010 | Richter et al. |
| 2010/0185275 | A1 | 7/2010 | Richter et al. |
| 2010/0249923 | A1 | 9/2010 | Alkhatib et al. |
| 2010/0262232 | A1 | 10/2010 | Annest |
| 2010/0280606 | A1 | 11/2010 | Naor |
| 2010/0298931 | A1 | 11/2010 | Quadri et al. |
| 2011/0112632 | A1 | 5/2011 | Chau et al. |
| 2011/0137409 | A1 | 6/2011 | Yang et al. |
| 2011/0172784 | A1 | 7/2011 | Richter et al. |
| 2011/0282438 | A1 | 11/2011 | Drews et al. |
| 2011/0313515 | A1 | 12/2011 | Quadri et al. |
| 2011/0319988 | A1 | 12/2011 | Schankereli et al. |
| 2011/0319989 | A1 | 12/2011 | Lane |
| 2011/0319990 | A1 | 12/2011 | Macoviak |
| 2012/0022639 | A1 | 1/2012 | Hacohen |
| 2012/0059450 | A1 | 3/2012 | Chiang et al. |
| 2012/0078353 | A1 | 3/2012 | Quadri et al. |
| 2012/0078360 | A1 | 3/2012 | Rafiee |
| 2012/0150290 | A1 | 6/2012 | Gabbay |
| 2012/0179086 | A1 | 7/2012 | Shank |
| 2012/0179244 | A1 | 7/2012 | Schankereli et al. |
| 2012/0215303 | A1 | 8/2012 | Quadri et al. |
| 2012/0316642 | A1 | 12/2012 | Yu et al. |
| 2012/0323316 | A1 | 12/2012 | Chau et al. |
| 2014/0018906 | A1 | 1/2014 | Rafiee |
| 2014/0039083 | A1 | 2/2014 | Krepski et al. |
| 2014/0046426 | A1* | 2/2014 | Kovalsky .............. A61F 2/2412 623/1.15 |
| 2014/0067054 | A1 | 3/2014 | Chau et al. |
| 2014/0128965 | A1 | 5/2014 | Rafiee |
| 2014/0163668 | A1 | 6/2014 | Rafiee |
| 2014/0324164 | A1 | 10/2014 | Gross |
| 2014/0343669 | A1 | 11/2014 | Lane et al. |
| 2014/0358223 | A1 | 12/2014 | Rafiee et al. |
| 2014/0379074 | A1 | 12/2014 | Spence |
| 2015/0119981 | A1* | 4/2015 | Khairkhahan ........ A61F 2/2466 |

FOREIGN PATENT DOCUMENTS

| | | | |
|---|---|---|---|
| WO | WO 2007/121314 | A2 | 10/2007 |
| WO | WO 2012/061809 | A2 | 5/2012 |
| WO | WO 2013/131069 | A1 | 9/2013 |
| WO | WO 2015/069947 | A1 | 5/2015 |
| WO | WO 2015/148821 | A1 | 10/2015 |

OTHER PUBLICATIONS

Patent Examination Report in related Australian patent application No. 2013205892, Oct. 13, 2015.
USPTO's Non-Final Office Action in related U.S. Appl. No. 13/886,983, Dec. 24, 2015.
International Search Report, for related application No. PCT/US2011/059586, mailed May 25, 2012.
International Preliminary Report on Patentability and Written Opinion, or related application No. PCT/US2011/059586, mailed May 25, 2012.
BioIntegral Surgical, Mitral Valve Restoration System, 2009.
Amendment filed Nov. 11, 2016 in U.S. Appl. No. 14/461,732.
Non-Final Office Action mailed Jun. 6, 2016 in U.S. Appl. No. 14/461,732.
Final Office Action mailed Dec. 14, 2016 in U.S. Appl. No. 14/461,732.
International Search Report for co-pending international application No. PCT/US2013/028774, mailed Jun. 14, 2013.
International Preliminary Report on Patentability and Written Opinion, on related application No. PCT/US2014/064431 mailed Mar. 26, 2015.
International Search Report, for related application No. PCT/US2015/022782, mailed Jun. 18, 2015.
Application and File Wrapper for U.S. Appl. No. 17/086,106, filed Oct. 30, 2020. Inventor: Rafiee.

* cited by examiner

Figure leaflets dual active fixation –full prosthesis– apical approach .

Figure leaflets dual active fixation – Hemi Prosthesis– apical approach .

Atrial above annulus View

- Novel Full Prosthesis (control)

- Novel Hybrid Prosthesis- A1 & A2

- Novel Hemi Prosthesis

Ventricle Sub-annulus view

Dashed lines represent PTFE on basic frame

Area within dashed lines represents ePTFE or other membrane material sewn into prosthesis Looking from front of hybrid toward the posterior circumference with PTFE PTFE sewn along dotted line; dashed line
Shows where PTFE in annular plane curves
Down to free edge Looking from front of hybrid toward the posterior circumference with PTFE Splits closed in the posterior leaflet during systole Top view

DEVICES, SYSTEMS AND METHODS FOR REPAIRING LUMENAL SYSTEMS

CROSS-REFERENCE TO RELATED APPLICATIONS

This patent application is a continuation of and claims the benefit of priority to U.S. patent application Ser. No. 17/086,106, filed Oct. 30, 2020, which in turn is a continuation-in-part of U.S. patent application Ser. No. 16/400,020, filed Apr. 30, 2019, now U.S. Pat. No. 11,839,543, which in turn is a continuation of and claims the benefit of priority to U.S. patent application Ser. No. 14/453,478, filed Aug. 4, 2014, now U.S. Pat. No. 10,449,046, which in turn is a continuation of and claims the benefit of priority to International Application No. PCT/US2014/49629, filed Aug. 4, 2014, which claims the benefit of priority to U.S. Provisional Patent Application Ser. No. 61/862,041, filed Aug. 4, 2013, U.S. Provisional Patent Application Ser. No. 61/878,264, filed Sep. 16, 2013 and U.S. Provisional Patent Application Ser. No. 62/007,369, filed Jun. 3, 2014.

This patent application is a continuation of and claims the benefit of priority to U.S. patent application Ser. No. 17/086,106, filed Oct. 30, 2020, which in turn is a continuation-in-part of and claims the benefit of priority to U.S. patent application Ser. No. 16/557,171, filed Aug. 30, 2019, now U.S. Pat. No. 11,357,627, which in turn is a continuation of U.S. patent application Ser. No. 15/413,017, filed Jan. 23, 2017, now U.S. Pat. No. 10,398,551, which in turn claims the benefit of priority to and is a continuation-in-part of U.S. patent application Ser. No. 14/074,517 filed Nov. 7, 2013, now U.S. Pat. No. 9,549,817, which in turn claims the benefit of U.S. Provisional Patent Application Ser. No. 61/723,734, filed Nov. 7, 2012. This patent application is also related to U.S. patent application Ser. No. 13/240,793, filed Sep. 22, 2011, International Application No. PCT/US2013/28774, filed Mar. 2, 2013, and International Application No. PCT/US2011/59586, filed Nov. 7, 2011. The entire contents of each of the above referenced patent applications is incorporated herein by reference for any purpose whatsoever.

BACKGROUND

Heart valves permit unidirectional flow of blood through the cardiac chambers to permit the heart to function as a pump. Valvular stenosis is one form of valvular heart disease that prevents blood from flowing through a heart valve, ultimately causing clinically significant heart failure in humans. Another form of valvular disease results from heart valves becoming incompetent. Failure of adequate heart valve closure permits blood to leak through the valve in the opposite direction to normal flow. Such reversal of flow through incompetent heart valves can cause heart failure in humans.

The human mitral valve is a complicated structure affected by a number of pathological processes that ultimately result in valvular incompetence and heart failure in humans. Components of the mitral valve include the left ventricle, left atrium, anterior and posterior papillary muscles, mitral annulus, anterior mitral leaflet, posterior mitral leaflet and numerous chordae tendonac. The anterior leaflet occupies roughly ⅔ of the mitral valve area whereas the smaller posterior leaflet occupies ⅓ of the area. The anterior mitral leaflet, however, hangs from the anterior ⅓ of the perimeter of the mitral annulus whereas the posterior mitral leaflet occupies ⅔ of the annulus circumference. Furthermore, the posterior mitral leaflet is often anatomically composed of three separate segments. In diastole, the anterior leaflet and the three posterior leaflets are pushed into the left ventricle opening the mitral orifice for blood to flow into the left ventricle. In systole, the leaflets are pushed toward the plane of the mitral annulus where the posterior leaflets and larger anterior leaflet come into coaptation to prevent blood flow from the left ventricle to the left atrium. The leaflets are held in this closed position by the chordac tendonae. Dysfunction or failure of one or more of these mitral components may cause significant mitral valvular regurgitation and clinical disease in humans.

Surgical treatment has been the gold standard since its introduction in the 1950s. Currently, there are two surgical options offered for treatment. The first, mitral valve replacement, requires complex surgery using cardiopulmonary bypass to replace the mitral valve using a mechanical or bioprosthetic valvular prosthesis. Although a time-tested and proven strategy for treatment, bioprostheic valves suffer from poor long-term durability and mechanical valves require anticoagulation. As an alternative, surgical mitral valve repair has emerged as a superior procedure to achieve mitral valve competence and normal function. This operation is really a collection of surgical techniques and prostheses that collectively are referred to a mitral valve repair. Each component of the mitral valve can be altered, replaced, repositioned, resected or reinforced to achieve mitral valve competence.

Mitral annuloplasty has become a standard component of surgical mitral valve repair. In performing this procedure, the circumference of the mitral valve annulus is reduced and/or reshaped by sewing or fixing a prosthetic ring or partial ring to the native mitral valve annulus. As a consequence of mitral annuloplasty, the posterior mitral leaflet often becomes fixed in a closed position, pinned against the posterior left ventricular endocardium. The opening and closure of the mitral valve is subsequently based almost entirely on the opening and closing of the anterior mitral valve leaflet.

SUMMARY

In accordance with one exemplary embodiment, a valve prosthesis is provided. The valve prosthesis may include a tubular member configured for deployment in a heart valve annulus, a first set of fastening mechanisms radially and outwardly disposed from the tubular member and configured to attach the valve prosthesis to cardiac tissue above the mitral valve annulus, a second set of fastening mechanisms radially and outwardly disposed from the tubular member and configured to attach the valve prosthesis to an incomplete circumference of left ventricular endocardium below the mitral annulus without impairing the opening or closing of the anterior mitral leaflet. The valve prosthesis may also include a partial covering of the internal area of the tubular member to simulate a fixed or mobile posterior mitral valve leaflet. The partial covering may be dynamically adjustable before, during or following implantation to correct mitral valve incompetence. The valve prosthesis may also include elements that traverse the diameter or a chord of the internal aspect of the tubular member to prevent prolapse of the anterior leaflet during systole.

Thus, in accordance with one embodiment, a valve prosthesis is provided. The prosthesis has a generally tubular body adapted for placement proximate a mitral annulus. The tubular body has a generally tubular upper portion adapted to substantially reside in the left atrium above the mitral annulus. The generally tubular upper portion has a first circumferential wall that is outwardly biased to urge against cardiac tissue of the left atrium. The tubular body also includes a lower portion extending downwardly from the generally tubular upper portion, the lower portion being configured to substantially reside in the left ventricle below the mitral annulus. The lower portion of this embodiment can be defined by an generally circumferential wall that extends downwardly from the generally tubular upper portion. The generally circumferential wall has a first circumferential end and a second circumferential end, and defines a circumferential extent therebetween. The generally circumferential wall extends along a posterior portion of the left ventricle. The first and second circumferential ends of the generally circumferential wall define a circumferential gap therebetween. The circumferential gap is preferably of sufficient circumferential extent to substantially prevent the prosthesis from interfering with the opening and closing of a native anterior mitral valve leaflet. The prosthesis further includes at least one prosthetic valve leaflet disposed within the tubular body, the at least one prosthetic valve leaflet being configured to occupy at least a portion of an opening defined by the generally tubular upper portion and the lower portion.

In accordance with further aspects, the at least one prosthetic valve leaflet can include at least one posterior prosthetic valve leaflet disposed proximate a posterior region of the prosthesis. The at least one posterior prosthetic valve leaflet can be configured to coapt with the native anterior mitral valve leaflet to close the mitral valve opening. The at least one posterior prosthetic valve leaflet can include a plurality of prosthetic leaflets. The plurality of prosthetic leaflets can be joined to each other to form a row of leaflets along a posterior portion of the valve prosthesis. If desired, the at least one posterior prosthetic valve leaflet can be substantially fixed. In other implementations, the at least one posterior prosthetic valve leaflet can be substantially movable.

In further implementations, the at least one prosthetic valve leaflet can include biological cells residing on the prosthetic material. If desired, the at least one prosthetic valve leaflet can include fabric. The fabric can include at least one of expanded PTFE, Dacron(R) polyester, and pericardium tissue. In some implementations, the at least one prosthetic valve leaflet can be substantially or fully formed from living tissue.

In accordance with further aspects of the disclosure, the circumferential extent of the generally circumferential wall of the lower portion, or downwardly depending posterior skirt, can be between about 90 degrees and about 270 degrees, about 120 degrees and about 240 degrees, about 150 degrees and about 210 degrees, or about 180 degrees, or any desired extent between about 90 and about 270 degrees in one degree increments. In accordance with a further aspect, the circumferential extent of the generally circumferential wall of the lower portion, also referred to herein and shown in the figures as a downwardly depending posterior skirt, can be configured to reside substantially between the commissures of the mitral valve along a posterior extent of the left ventricle.

In accordance with a further aspect, the prosthesis can form an open channel in the mitral annulus, and the at least one prosthetic valve leaflet can be provided in a separate mechanism, for example, that is attached to the prosthesis body before or after delivering the prosthesis to the mitral valve.

In accordance with yet a further aspect, the prosthesis can further include at least one transverse support extending from a first lateral portion of the prosthesis to an opposing, second lateral portion of the prosthesis to prevent prolapse of an anterior native leaflet during systole. The at least transverse support can include at least one of Dacron® polyester material, expanded PTFE and pericardium tissue.

In some implementations, the prosthesis can further include at least one circumferential inflatable bladder disposed along a portion of the generally circumferential wall of the lower portion, the bladder being configured to inflate outwardly from the generally circumferential wall of the lower portion and against a surface of the left ventricle to prevent flow around the outside of the valve prosthesis. If desired, the prosthesis can further include at least one circumferential inflatable bladder disposed within a portion of the generally circumferential wall of the lower portion, the inflatable bladder being configured to inflate outwardly to cause the generally circumferential wall of the lower portion to urge against an inner surface of the left ventricle to prevent flow around an outer portion of the valve prosthesis. The at least one circumferential bladder can include a plurality of adjacent chambers that can be inflated individually. The plurality of adjacent cells can be arranged circumferentially about the periphery of the generally circumferential wall of the lower portion.

In accordance with further aspects, the prosthesis can further include a plurality of radially distributed fasteners disposed proximate the generally tubular upper portion for helping to maintain the position of the valve prosthesis within the mitral annulus. The fasteners can be within and at least partially define the shape of the generally tubular upper portion. The fasteners can cooperate to cause the generally tubular upper portion to form a funnel shape. The fasteners can be adapted to urge against the walls of the left atrium. If desired, the fasteners can be configured to cause the generally tubular upper portion to form a bell shape. If desired, the fasteners can urge against the atrial side of the mitral annulus. In further implementations, the prosthesis can further include at least one lower fastener disposed proximate the generally circumferential wall of the lower portion, the at least one lower fastener being configured to hold the valve prosthesis in place. The at least one lower fastener can include a plurality of fasteners formed into the generally circumferential wall of the lower portion. If desired, the at least one lower fastener can include at least one fastener disposed radially outwardly from the generally circumferential wall of the lower portion. The at least one lower fastener can be adapted to urge upwardly against the ventricular side of the mitral annulus.

In accordance with further aspects, the valve prosthesis can further include at least one guiding conduit for receiving a delivery rail. The at least one guiding conduit can be configured to permit the valve prosthesis to be guided along the rail to facilitate installation of the valve prosthesis. In some implementations, the generally tubular upper portion can have a "D" shaped cross section formed by a substantially flat wall configured to engage the atrial anterior wall above the native anterior mitral valve leaflet, and a substantially curved wall configured to engage the posterior left atrial wall. The at least one posterior prosthetic valve leaflet can have a curved lateral profile in an anterior-posterior plane within the prosthesis, such that the at least one posterior valve leaflet curves downwardly along a posterior-anterior direction. In further implementations, the valve prosthesis can define a saddle-shaped engagement surface for engaging with a posterior portion of the mitral annulus and an anterior portion of the left atrium above the native anterior mitral valve leaflet, the engagement surface having a "D" shaped projection in a plane substantially parallel to the mitral annulus.

The disclosure also provides a valve prosthesis having a curved body adapted for placement proximate a mitral annulus. The curved body has a generally curved planar upper portion adapted to substantially reside in a posterior region of the left atrium above the mitral annulus, the generally curved planar upper portion having a first circumferential wall that is outwardly biased to urge against cardiac tissue of the posterior of the left atrium, and a lower portion extending downwardly from the generally curved planar upper portion, the lower portion being configured to substantially reside in the left ventricle below the mitral annulus. The lower portion is defined by an generally circumferential wall that extends downwardly from the generally curved planar upper portion. The generally circumferential wall has a first circumferential end and a second circumferential end defining a circumferential extent therebetween. The generally circumferential wall extends along a posterior portion of the left ventricle. The first and second circumferential ends of the generally circumferential wall define a circumferential gap therebetween, the circumferential gap being of sufficient circumferential extent to substantially prevent the prosthesis from interfering with the opening and closing of a native anterior mitral valve leaflet. The prosthesis further includes at least one prosthetic valve leaflet disposed within the curved body. The at least one prosthetic valve leaflet is configured to occupy at least a portion of an opening defined by the generally curved planar upper portion and the lower portion.

In accordance with further aspects, the at least one prosthetic valve leaflet can include at least one posterior prosthetic valve leaflet disposed proximate a posterior region of the prosthesis. The at least one posterior prosthetic valve leaflet is preferably configured to coapt with the native anterior mitral valve leaflet to close the mitral valve opening. The at least one posterior prosthetic valve leaflet can include a plurality of prosthetic leaflets. The plurality of prosthetic leaflets can be joined to each other to form a row of leaflets along a posterior portion of the valve prosthesis. The at least one posterior prosthetic valve leaflet can be substantially fixed or movable. If desired, the at least one prosthetic valve leaflet includes biological cells residing on the prosthetic material. The at least one prosthetic valve leaflet can include fabric. The fabric can include at least one of expanded PTFE, Dacron(R) polyester, and pericardium tissue. If desired, the at least one prosthetic valve leaflet can be substantially or entirely formed from living tissue.

In some implementations, the circumferential extent of the generally circumferential wall of the lower portion (and/or of the generally curved planar upper portion) can be, for example, between about 90 degrees and about 270 degrees, between about 120 degrees and about 240 degrees, between about 150 degrees and about 210 degrees, or about 180 degrees, or any desired extent between about 90 and about 270 degrees in one degree increments. The circumferential extent of the generally circumferential wall of the lower portion can be configured to reside substantially between the commissures of the mitral valve along a posterior extent of the left ventricle. The prosthesis can form an open channel in the mitral annulus, and the at least one prosthetic valve leaflet can be provided in a separate mechanism.

If desired, the valve prosthesis can further include at least one transverse support extending from a first lateral portion of the prosthesis to an opposing, second lateral portion of the prosthesis to prevent prolapse of an anterior native leaflet during systole. The at least transverse support can include at least one of Dacron® polyester material, expanded PTFE and pericardium tissue, among others. If desired, the valve prosthesis can further includes at least one circumferential inflatable bladder disposed along a portion of the generally circumferential wall of the lower portion, or downwardly depending posterior skirt. The bladder can be configured to inflate outwardly from the generally circumferential wall of the lower portion, or downwardly depending posterior skirt, and against a surface of the left ventricle to prevent flow around the outside of the valve prosthesis. If desired, the inflatable bladder can be configured to inflate outwardly to cause the generally circumferential wall of the lower portion to urge against an inner surface of the left ventricle to prevent flow around an outer portion of the valve prosthesis. If desired, the at least one circumferential bladder can include a plurality of adjacent chambers that can be inflated individually. The plurality of adjacent cells can be arranged circumferentially about the periphery of the generally circumferential wall of the lower portion.

In some implementations, the valve prosthesis can further include a plurality of radially distributed fasteners disposed proximate the generally curved planar upper portion to help maintain the position of the valve prosthesis within the mitral annulus. The plurality of radially distributed fasteners can be disposed within and at least partially define the shape of the generally curved planar upper portion. The fasteners can cooperate to cause the generally curved planar upper portion to form a funnel shape. The fasteners can be adapted to urge against the posterior wall of the left atrium. The fasteners can cooperate to cause the generally curved planar upper portion to form a bell shape. The fasteners can urge against the atrial side of the mitral annulus.

In some implementations, the prosthesis can further include at least one lower fastener disposed proximate the generally circumferential wall of the lower portion. The at least one lower fastener can be configured to hold the valve prosthesis in place. The at least one lower fastener can include a plurality of fasteners formed into the generally circumferential wall of the lower portion. The at least one lower fastener can include at least one fastener disposed radially outwardly from the generally circumferential wall of the lower portion. The at least one lower fastener can be adapted to urge upwardly against the ventricular side of the mitral annulus.

In some implementations, the valve prosthesis can further include at least one guiding conduit for receiving a delivery rail. The at least one guiding conduit can be configured to permit the valve prosthesis to be guided along the rail to facilitate installation of the valve prosthesis. The at least one posterior prosthetic valve leaflet can have a curved lateral profile in an anterior-posterior plane within the prosthesis, such that the at least one posterior valve leaflet curves downwardly along a posterior-anterior direction. If desired, the valve prosthesis can define a partial saddle-shaped engagement surface for engaging with a posterior portion of the mitral annulus.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 4C further depicts the access direction in dotted lines in the case of atrial percutaneous delivery.

FIG. 19(A) reveals that the lateral wall of the tubular element of the exemplary prosthesis abuts the mitral annulus for a circumference of the mitral annulus except where the anterior mitral leaflet emanates from the anterior mitral annulus between the right and left commissures. FIG. 19(B) reveals that the first and second sets of atrial and ventricular radially and outwardly disposed fixation elements may contact each other in the plane of the mitral annulus between the mitral annulus and the tubular element of the device for less than the entire circumference of the mitral orifice (2), leaving the circumference of the mitral annulus subtending the anterior mitral valve leaflet free (1).

DETAILED DESCRIPTION

Exemplary embodiments provide systems, devices and methods for repairing or replacing elements of the mitral valve. Exemplary elements of the valve prosthesis include the device frame, prosthetic posterior mitral leaflet equivalent and elements to prevent or reduce abnormal prolapse of the native anterior mitral leaflet during systole. Exemplary methods of implanting the valve prosthesis include direct open surgical placement, minimally invasive surgical placement either with or without the use of cardiopulmonary bypass, and totally catheter based implantation. Exemplary methods for maintaining the valve prosthesis in the preferred mitral annular location include external compression, compression following rail or suture guided implantation and seating with subsequent active or passive fixation of the valve prosthesis based upon the rail or suture guides.

Valve Device Frame

Figure 1:
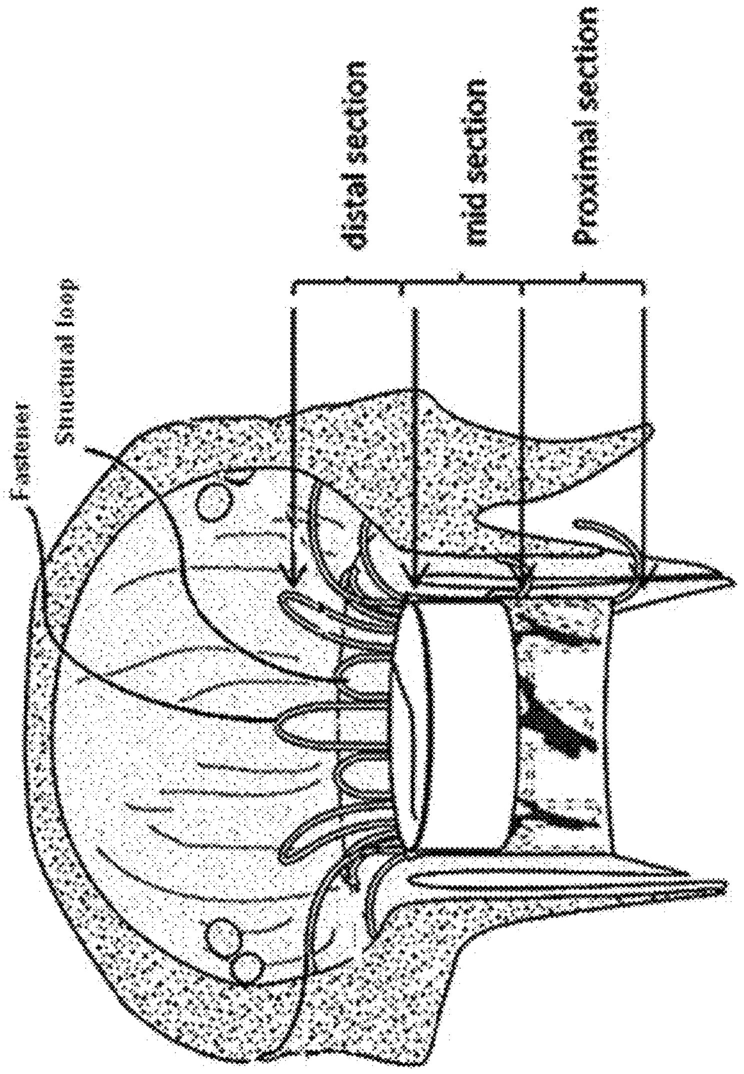
FIG. 1 illustrates a cross-sectional view taken through a mitral valve in which an exemplary valve prosthesis is deployed at the annulus of the mitral valve. As illustrated, the prosthesis includes a framework formed from a combination of structural loops that may also act as fasteners that can help hold the prosthesis in place. As illustrated, the prosthesis includes a proximal section in the ventricle, a mid section including a valve, and a distal section in the atrium. The posterior aspects of the anatomy are illustrated, but the anterior aspects of how the prosthesis interacts with the anatomy are discussed below.
Figure 2:
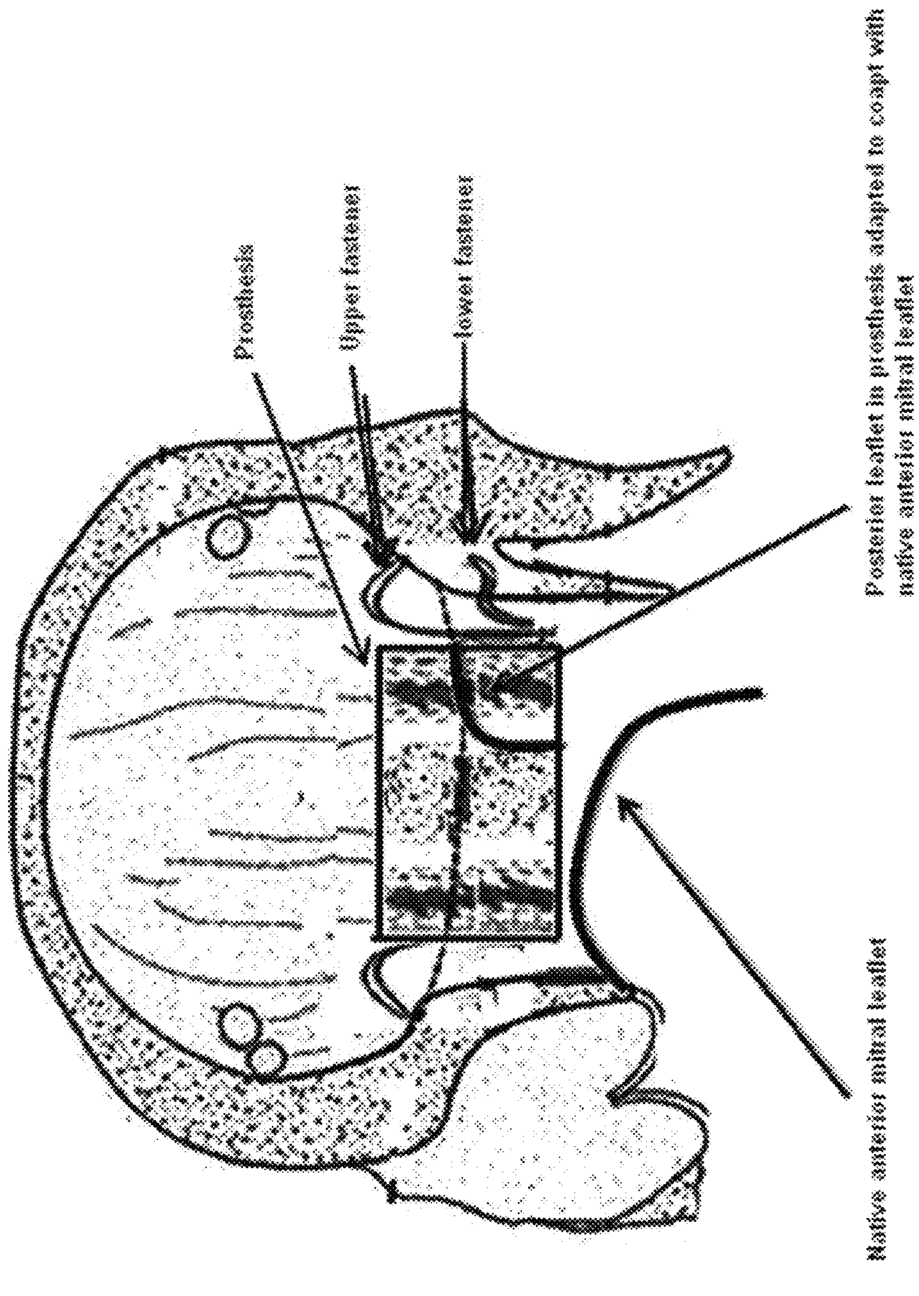
FIG. 2 illustrates a cross-sectional view through the mitral valve, illustrating the native anterior mitral leaflet with an exemplary valve prosthesis deployed at the annulus (dotted lines) with the native anterior mitral leaflet free to coapt against the prosthetic posterior mitral leaflet as described herein. Also illustrated are fasteners located on an upper generally tubular portion of the prosthesis, and fasteners located on a downwardly extending ventricular skirt of the prosthesis.
Figure 3:
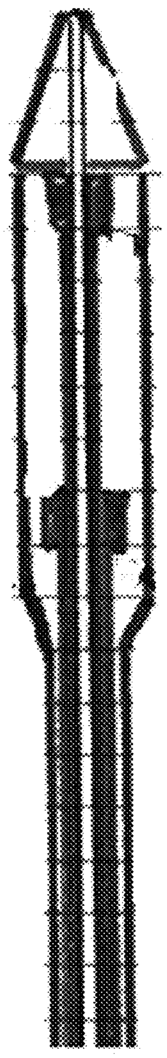
FIG. 3 illustrates a longitudinal cross-sectional view of an exemplary prosthesis mounted within an exemplary catheter delivery device.
Figure 4B:
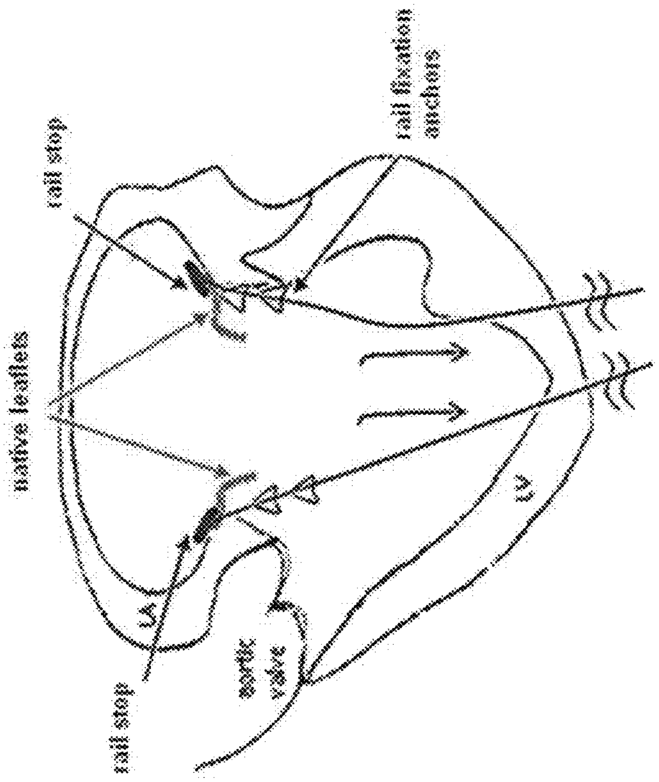
FIGS. 4A-E-illustrate exemplary aspects of delivering the valve prosthesis from either a left atrial or ventricular approach with or without guided fixation to the mitral annulus. For example, with respect to FIG. 4C, a mitral valve prosthesis is provided having a lower circumferential edge and an upper circumferential edge defining a generally cylindrical body therebetween defined by a plurality of loops connected to a membrane. The body may be tapered along its length and/or have flared ends, as desired, as described herein. The prosthesis, as illustrated, further includes one or more tethers. Prosthesis is installed by advancing it along rails to its final location.
Figure 4A:
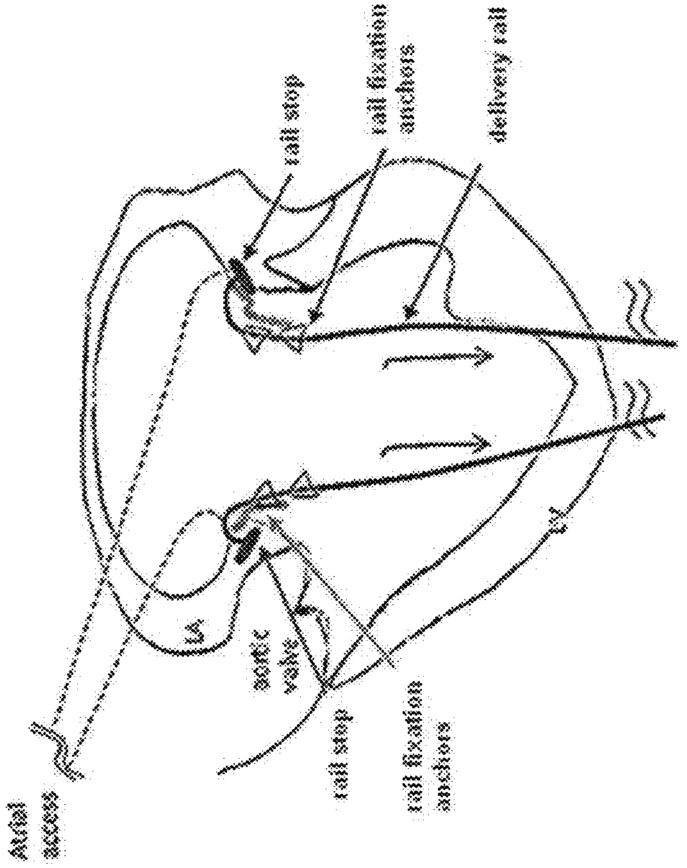
Figure 4C:
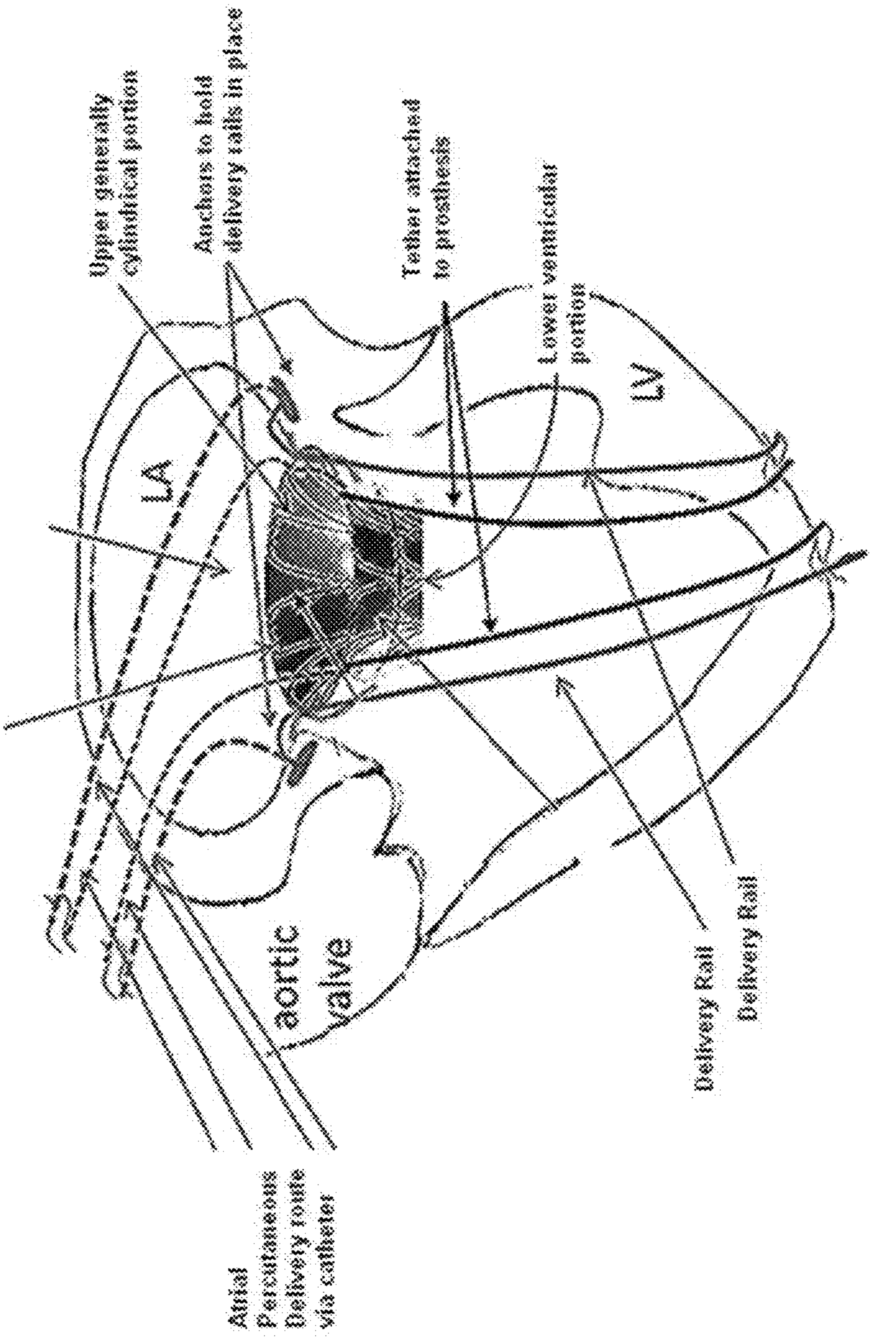
Figure 4D:
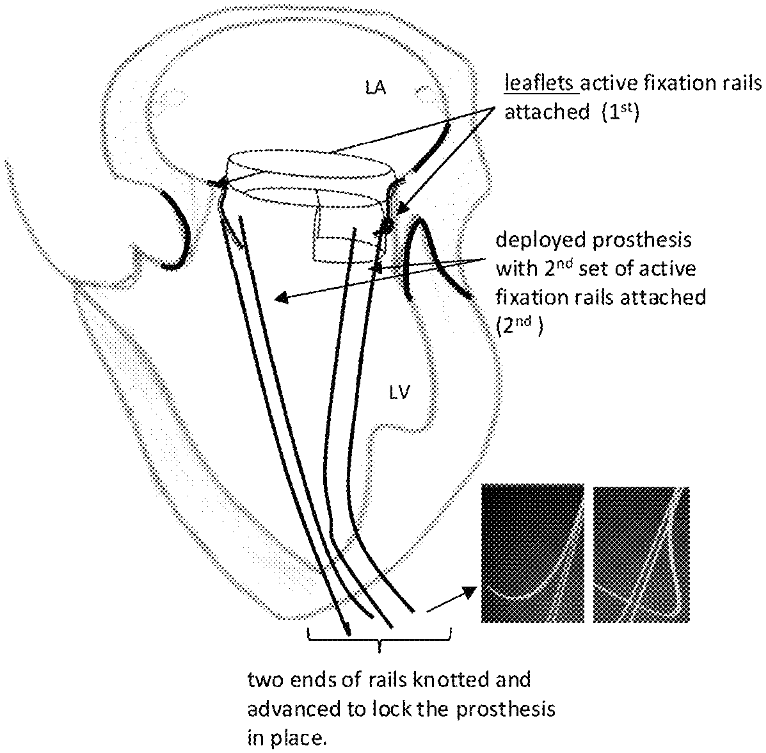
Figure 4E:
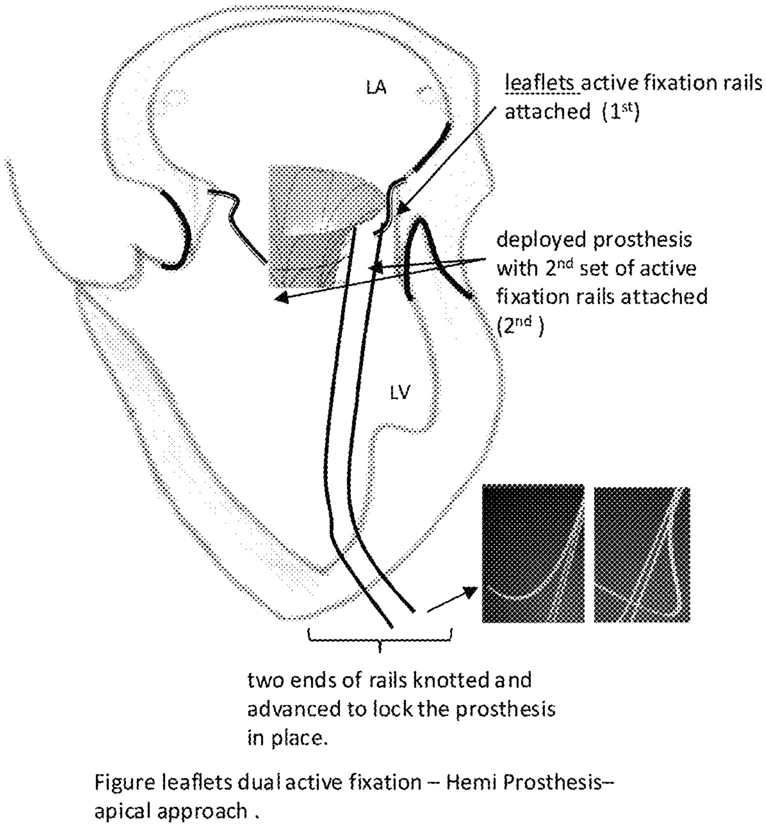
Figure 5A:
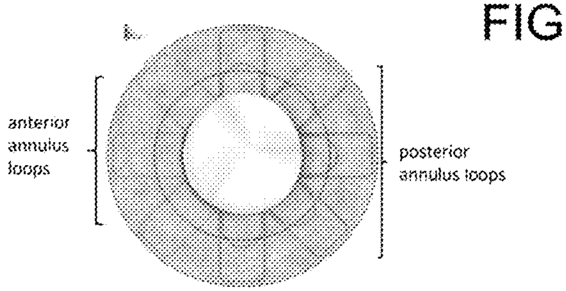
FIG. 5A-G illustrates various aspects of the designs of different valve prostheses.
Figure 5B:
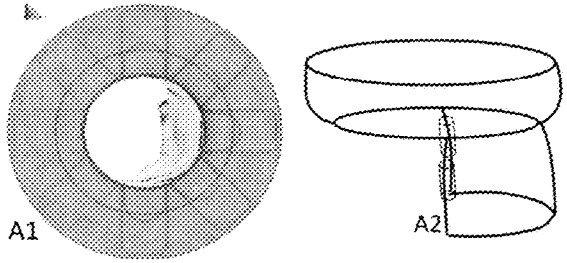
Figure 5C:
Figure 5D:
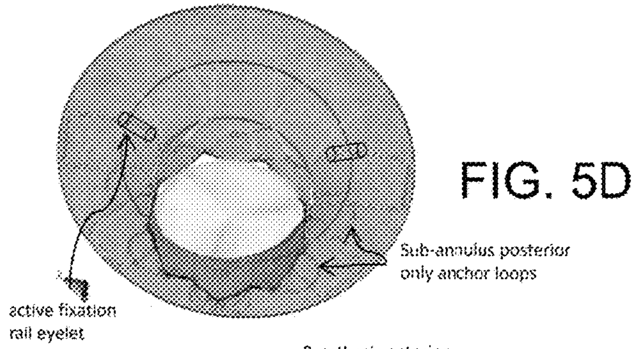
Figure 5E:
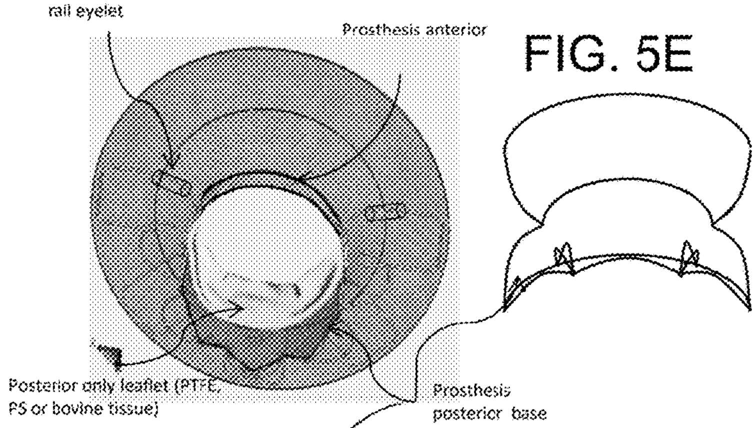
Figure 5F:
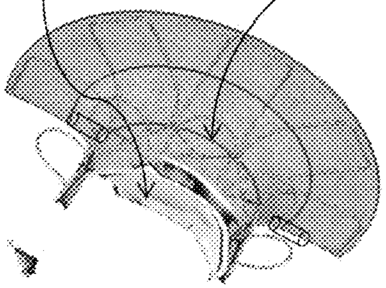
Figure 5G:
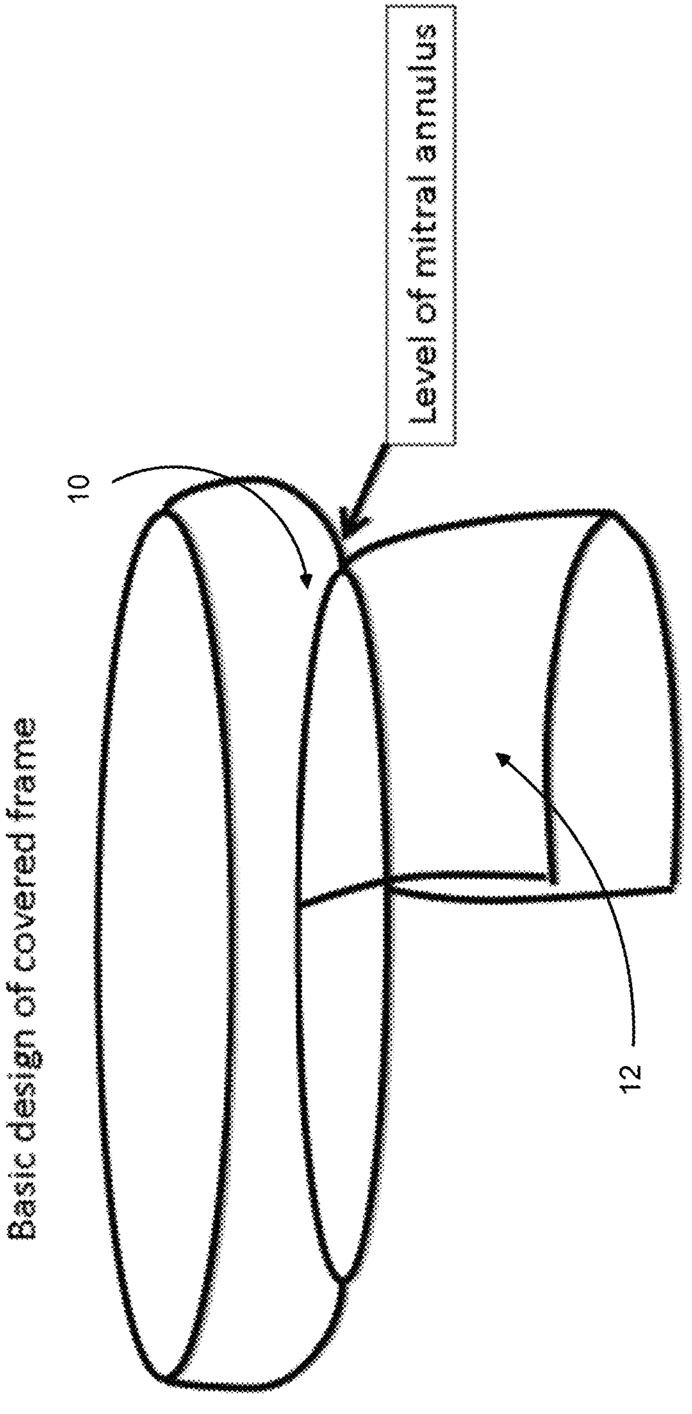
Figure 6:
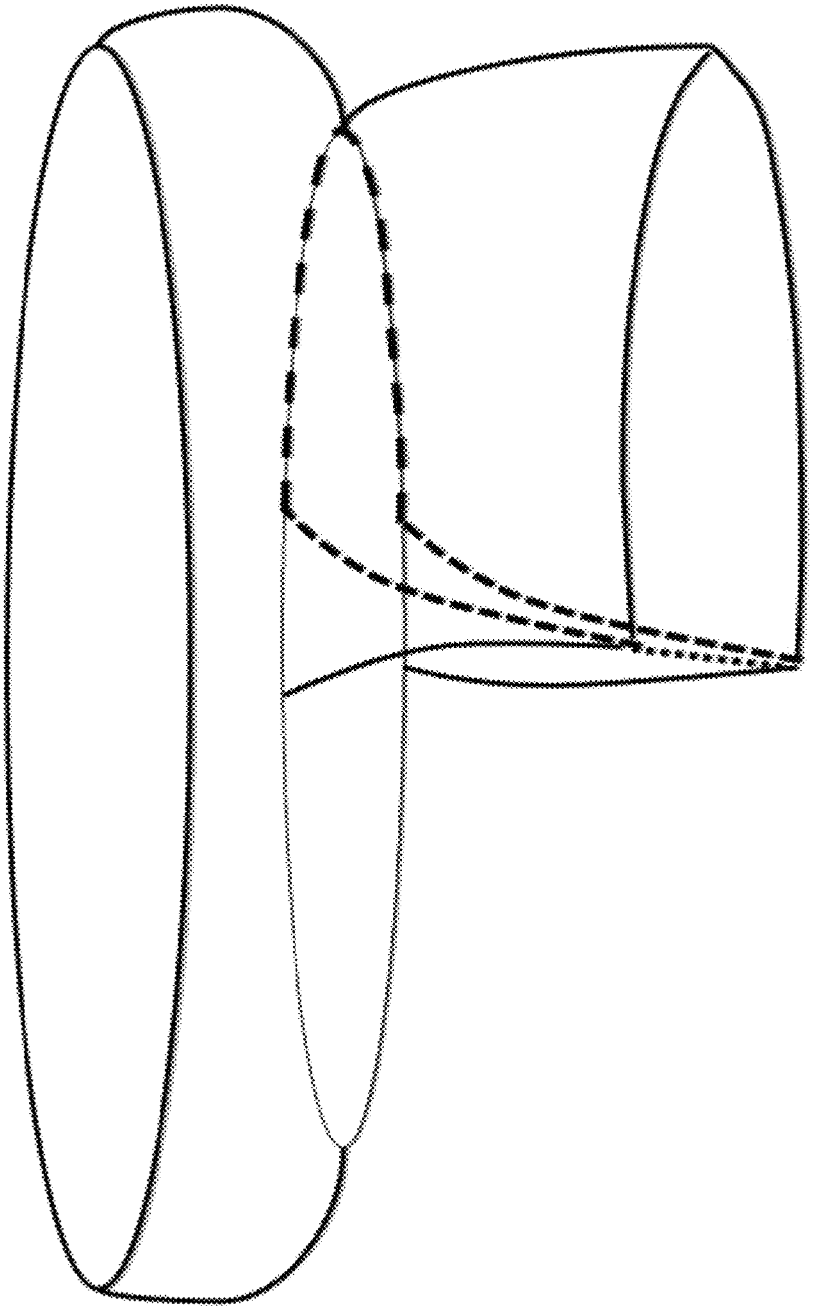
FIG. 6 illustrates an exemplary frame of the valve prosthesis with an exemplary prosthetic posterior mitral leaflet equivalent positioned within the frame.
Figure 7:
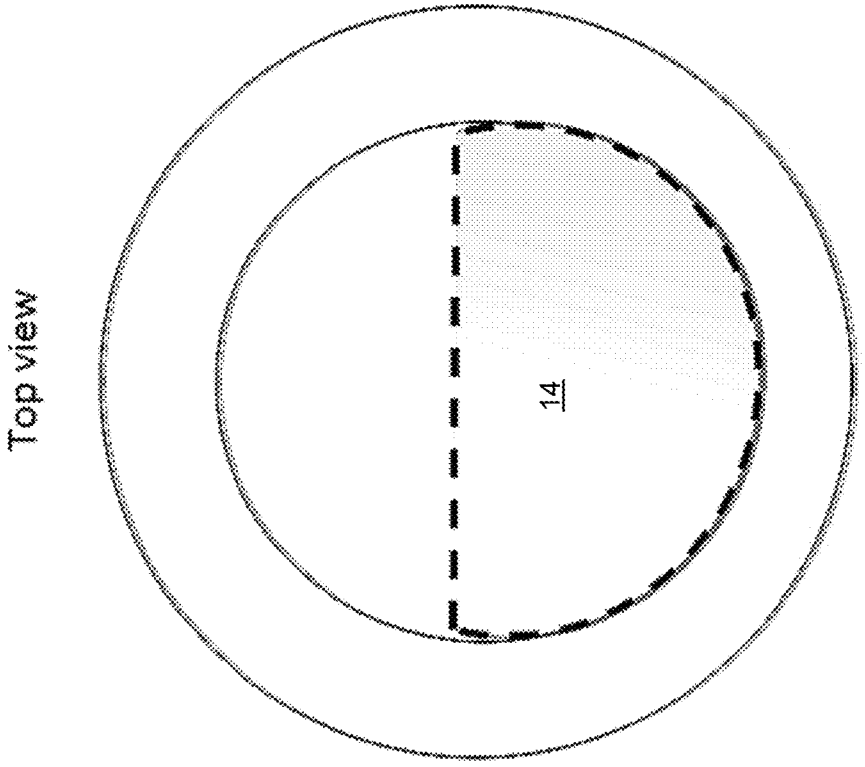
FIG. 7 illustrates a top-down view of an exemplary valve prosthesis with an exemplary prosthetic posterior leaflet in position covering a subtotal area of the tubular member of the prosthesis.
Figure 8:
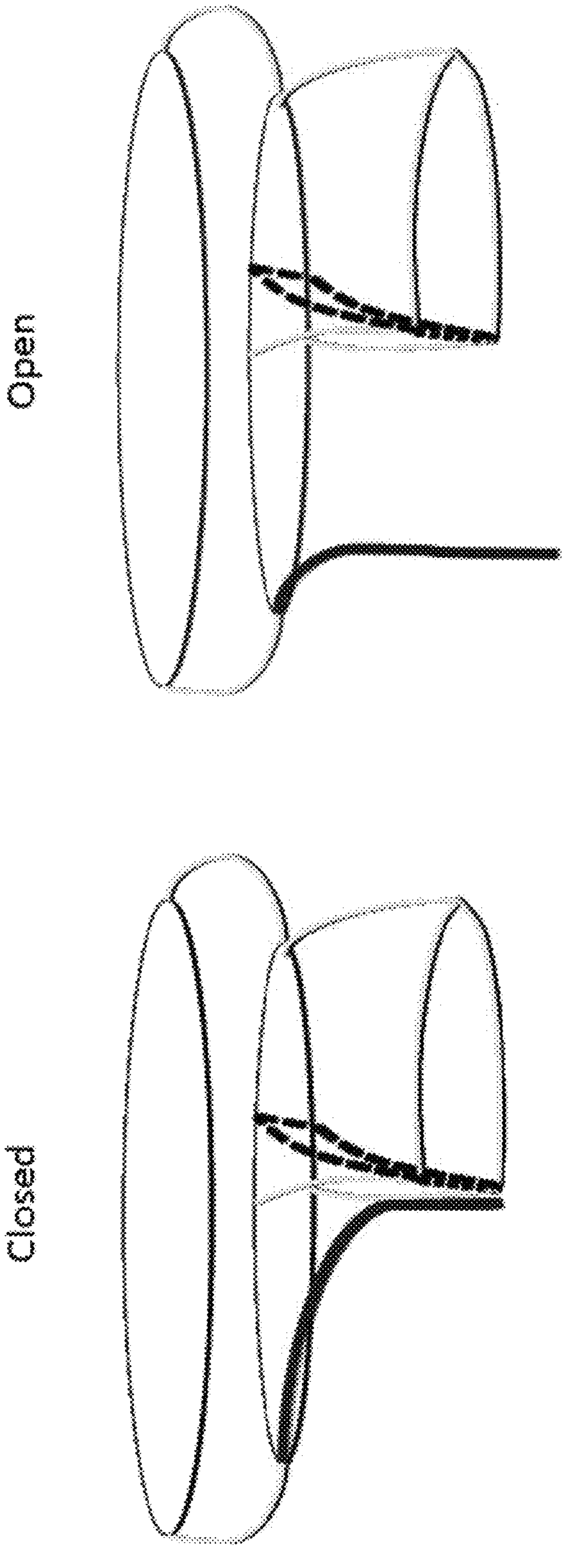
FIG. 8 illustrates how an exemplary valve prosthesis would allow the native anterior mitral valve leaflet to coapt with the prosthetic posterior mitral leaflet during valve closure in systole and open away from an exemplary prosthetic posterior mitral leaflet in diastole.
Figure 9:
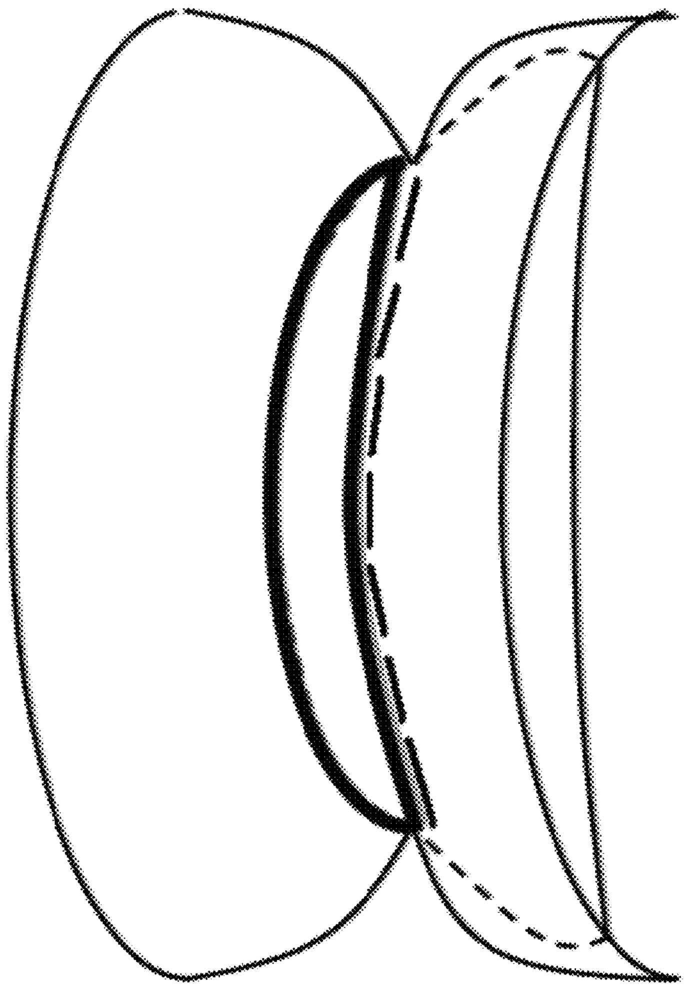
FIG. 9 illustrates a cross-sectional view of an exemplary prosthesis with an exemplary fixation of the prosthetic posterior mitral leaflet fixed along the mitral plane posteriorly, and more anteriorly down into the ventricular section of the device to its margin.
Figure 10:
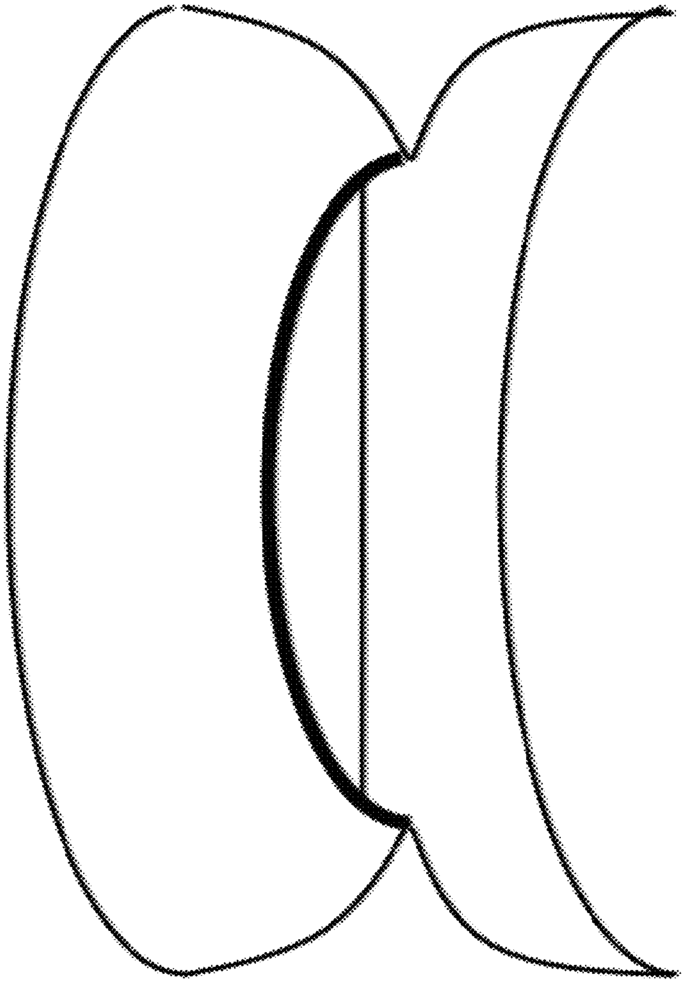
FIG. 10 illustrates a cross-sectional view of an exemplary prosthesis with an exemplary fixation of the prosthetic posterior mitral leaflet fixed entirely in the plane of the mitral annulus.
Figure 11:
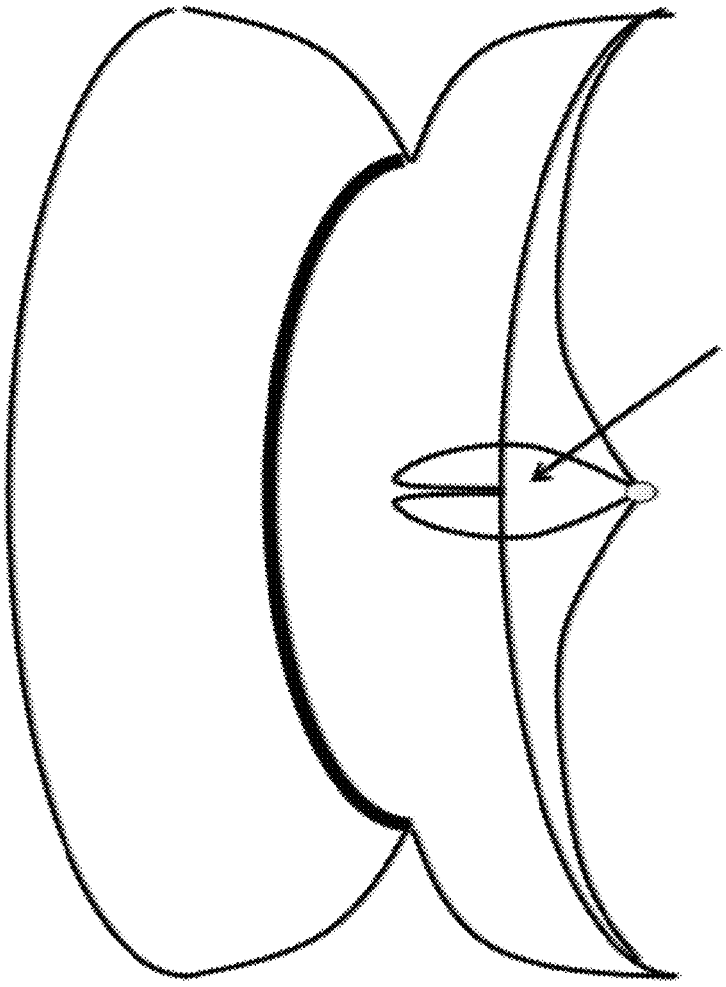
FIGS. 11 and 12 illustrate cross-sectional views of an exemplary prosthesis with an exemplary design of the prosthetic posterior mitral leaflet in two sections with the ability to move into (FIG. 12) and out of (FIG. 11) the position of coaptation with the native anterior mitral leaflet to facilitate left ventricular filling during diastole. In an exemplary state, the prosthetic posterior leaflets could be fixed by a tethering mechanism to the ventricular fastening mechanisms to prevent prolapse of the prosthetic posterior leaflet or leaflets during systole.
Figure 12:
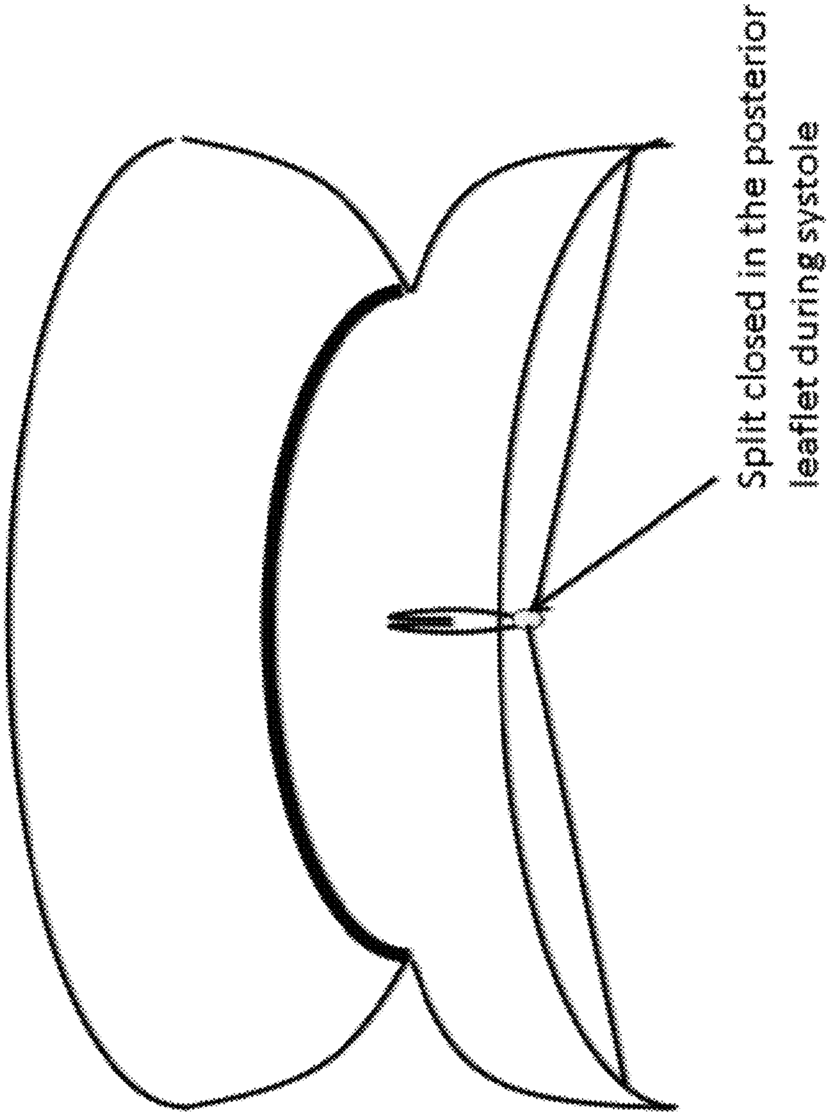
Figure 13:
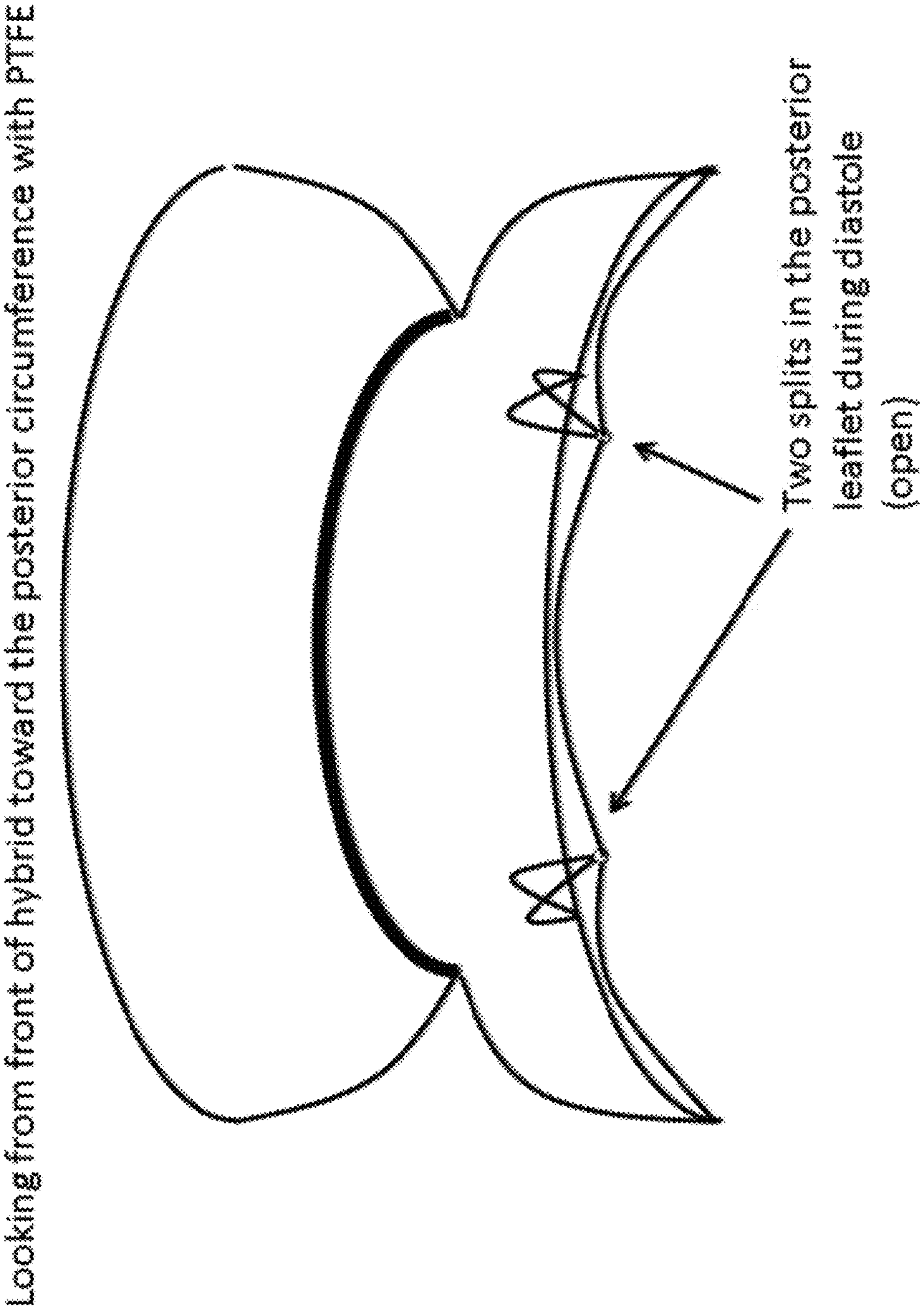
FIGS. 13 and 14 illustrate cross-sectional views of an exemplary prosthesis with an exemplary design of the prosthetic posterior mitral leaflet in three sections with the ability to move into (FIG. 14) and out of (FIG. 13) the position of coaptation with the native anterior mitral leaflet to facilitate left ventricular filling during diastole.
Figure 14:
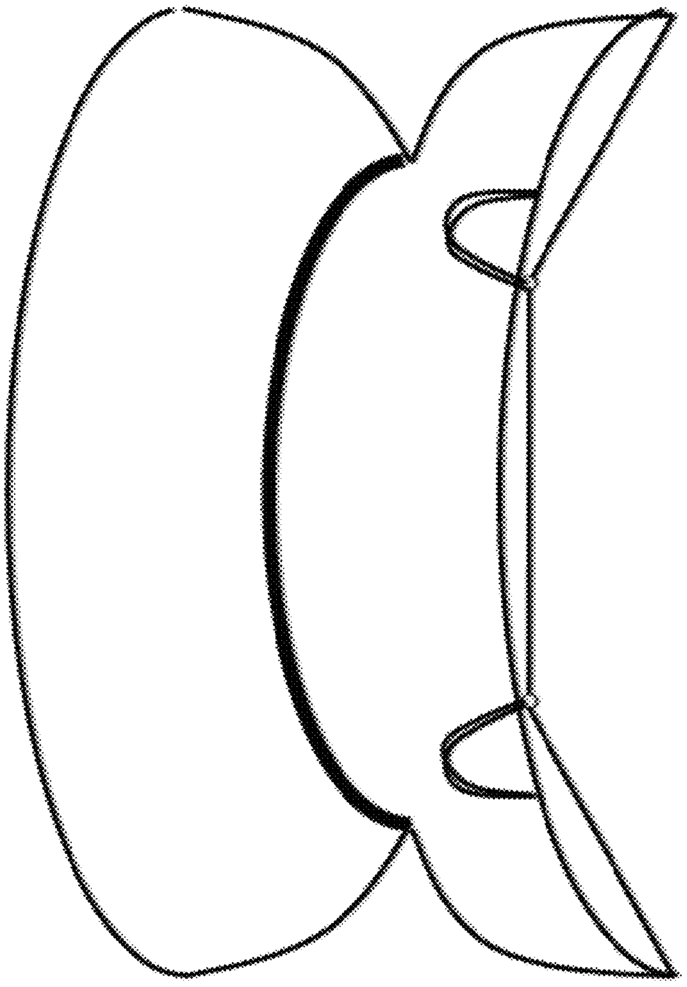

Exemplary embodiments on the frame of the valve prosthesis depicted in the Figures include a central element that can be inserted within the mitral valve annulus with elements (e.g., struts, loops and the like) above and below the central element to provide for fixation of the central element in the annulus. In one embodiment of the central element of the valve device (FIGS. 5C, 5F), the prosthesis can be tubular or "D" shaped with the flat portion subtending the atrial side of the anterior annulus between the right and left fibrous trigones with the curved portion of the "D" to subtend the posterior annulus between the trigones. Either the anterior portion of the "D" shaped device, or the posterior portion of the "D" shaped device, or both sections can be distensible and therefore capable of shortening or lengthening to adjust variably to different size mitral annulae. This describes a prosthesis design that is form fitting and/or size adjustable to the shape of the mitral annulus of individual hearts by virtue of design.

The tubular element may be planar or may be shaped planar for a section of the tubular element but with an elevation of one section of the circumference of the tubular element that corresponds to the anterior (atrial) portion of the tubular element of the device. The advantage of such an asymmetrical shape can be that it simulates the natural "saddle" shape of the mitral valve orifice. This shape can allow for radial compression and seating of the valve prosthesis above the mitral annulus subjacent to the anterior mitral leaflet on the atrial side of the device. This exemplary shape can provide for unimpaired excursion of the anterior mitral leaflet to allow adequate opening and closure of the mitral valve orifice based on the movement of the anterior leaflet.

In an alternative embodiment of the tubular or D-shaped member, the anterior circumference of the device can be flat or semicircular, while the remainder of the circumference can remain circular. The anterior section of the device may expand to match the distance between the right and left fibrous trigones of the native mitral annulus. Such a feature can allow one device to fit into differing size mitral annulae.

Figure 18:
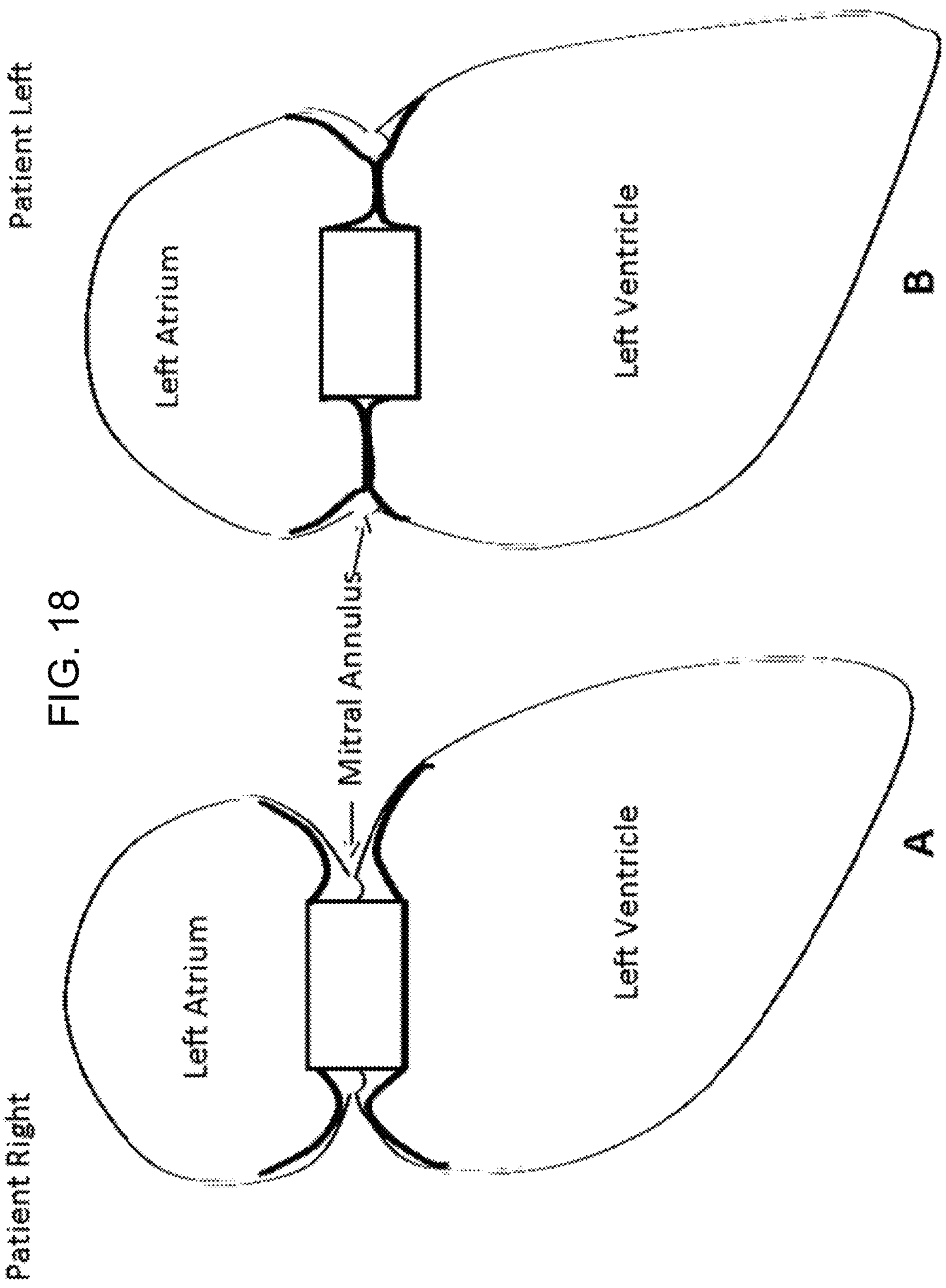
FIG. 18 illustrates a longitudinal cross-sectional view of en exemplary prosthesis deployed in the mitral annulus in a heart with a non-dilated (A) and a dilated (B) mitral annulus. These figures together illustrate a feature of an exemplary prosthesis whereby the first and second sets of atrial and ventricular radially and outwardly disposed fixation elements may act entirely to provide compression fixation of the tubular element of the prosthesis in the mitral annulus through force on the endocardium of the atrium and ventricle, respectively (A). Alternatively, the first and second sets of atrial and ventricular radially and outwardly disposed fixation elements may contact each other in the plane of the mitral annulus for a portion of the circumference of the mitral annulus as well as providing compression fixation of the tubular element of the prosthesis in the mitral annulus through force on the endocardium of the atrium and ventricle laterally, respectively (B).
Figure 19:
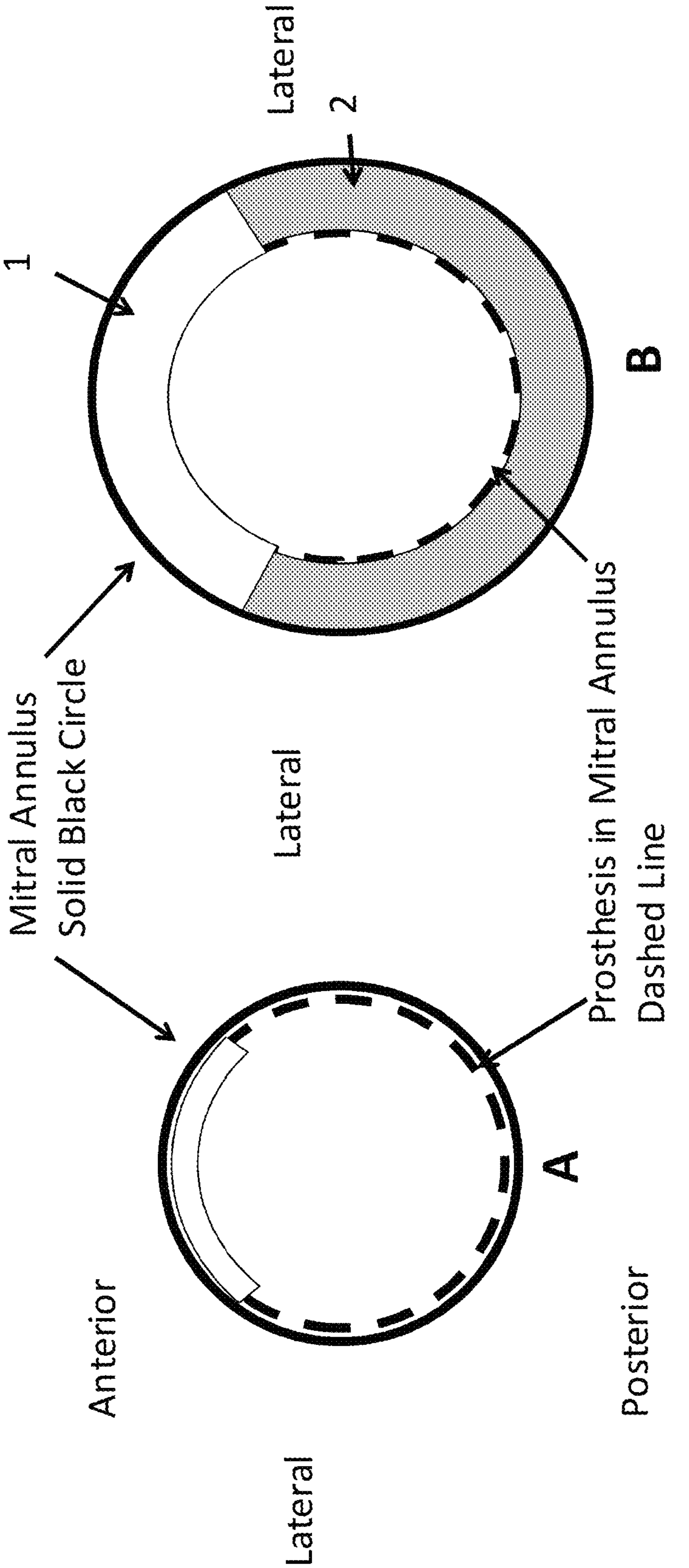
FIG. 19 illustrates a cross-section through a non-dilated (A) mitral annulus and a dilated (B) mitral annulus with the exemplary prosthesis of FIG. 18 in place.

In a further alternative embodiment (e.g., FIG. 18), the first set of radially and outwardly disposed fixation elements can abut the atrial endocardium above the mitral annulus, holding the tubular element of the device at or above the plane of the mitral annulus. Along the anterior mitral annulus, where the anterior mitral valve attaches to the annulus between the anterior and posterior mitral commissures, the tubular element can be above the annulus. The second set of radially and outwardly disposed fixation elements can be configured to abut the ventricular endocardium along the posterior mitral annulus between the anterior and posterior mitral commissures to provide compression and hold the tubular element at or near the plane of the mitral annulus posteriorly. It is a feature of this embodiment that the first set of fixation elements and second set of fixation elements can abut each other in the plane of the mitral annulus between the anterior and posterior mitral commissures along the posterior mitral annulus. This embodiment can provide a mechanism to utilize the prosthesis to reduce the orifice size of the mitral valve to that of the tubular element of the device. This feature can be used, for example, to treat patients with mitral regurgitation exclusively or partially related to native mitral annular dilatation in conjunction with other prosthesis elements described herein.

An exemplary embodiment of the ventricular portion of the device can include an incomplete circumference designed to provide for compression against the left ventricular endocardium and fixation of the tubular element of the valve device at or above the mitral annulus. This shape and positioning of the valve device can permit unobstructed opening and closing motion of the anterior mitral leaflet. The ventricular posterior of the valve device would theoretically compress the posterior mitral leaflet against posterior left ventricular endocardium when fully deployed.

An exemplary embodiment of the atrial section of the device can expand to coapt with the endocardium of the left atrium to provide for fixation of the tubular section of the valve device at or above the mitral annulus. When the atrial and ventricular sections of the device are fully deployed, the tubular or D-shaped element of the device can occupy the mitral annular plane, or can occupy the mitral annulus and extend into the left atrium and left ventricle for a desired distance.

An exemplary method of fixation of the valve device can include compression or the radial force exerted on the left atrial endocardium, mitral annulus and left ventricular endocardium by the expanded and fully deployed valve device. The atrial section of the device adjacent to the anterior mitral annulus would be held in position by radial force and/or by two points of fixation at the fibrous trigones and/or other points along the circumference of the annulus.

An alternate exemplary embodiment of fixation of the valve device at the mitral annular level can be performed by active fixation. Here, barbed arrows or other fasteners can extend radially and outwardly from the tubular element of the valve device to project into the anterior annulus or trigones once the device is deployed. Alternately, hooks or other fasteners can extend radially from the ventricular side of the tubular element to directly engage the anterior annulus at the anterior and posterior commissures posterior to the trigones. Alternatively, barbed spears or hooks or other fasteners can extend radially and outwardly from either the ventricular or atrial fastening members during or after implantation.

One embodiment of the device can include one or more inflatable chambers located on the outer circumference of the central tubular element of the device. The chambers can be filled with liquid or gas or semisolid material remotely or through directly connected tube(s) to cause the inflatable chambers to expand and occupy space between the external central (annular) plane of the device and the native mitral annulus. Such a device can help prevent periprosthetic leak, for example, in the setting of a calcified, irregularly shaped mitral annulus.

In another embodiment of the device, some or all of the frame of the device can be composed of biological tissue and/or tissue permitting tissue ingrowth (e.g., ePTFE). This composition of the device can allow for fixation of the device into the mitral annulus initially through compression with or without active fixation. Over time, the biological tissue would permit growth into the native annulus, left atrium and/or left ventricle where fixation based on compression would no longer be necessary.

Prosthetic Posterior Leaflet Equivalent

An exemplary embodiment of a valve device can include a covering of the central tubular element of the device to create an artificial posterior mitral leaflet connected by a variety of fixation techniques to the posterior circumference of the device. The covering can be of a variety of Artificial or biological tissue compatible types as disclosed elsewhere herein, for example. The covering, or prosthetic posterior mitral leaflet, can either be attached in a fixed or stationary position, or loosely to provide for both an opening and a closing position. The covering can be composed of either a single or multiple covering pieces. The single or multiple covering pieces can be connected to the inside of the device in an annular plane along the posterior circumference of the device not occupied by the anterior mitral leaflet when the anterior mitral leaflet would be in a closed position. The single covering version of the device can have the covering connected to the ventricular fixation portion of the device at the incomplete margin, along the internal aspect of the ventricular fixation element toward the tubular element and then along the annular plane within the tubular element posteriorly. In the double or multiple covering versions, the coverings can be connected to the inner annular portion of the device as above, with sectional coverings held by connecting cords to the ventricular fixation element posteriorly along the base to prevent prolapse above the plane of the tubular element.

In one embodiment, the length and/or height of the artificial posterior covering of the device can be controlled before, during or after device implantation. In a particular embodiment, two ends of one string can run under the posterior mitral covering along the edge to alter the tension and therefore the area of the mitral orifice covered by the posterior covering. Similar mechanisms can provide for altering the shape and circumference covered by the prosthetic posterior mitral leaflet.

In one embodiment of the prosthetic posterior mitral leaflet, the single covering version can include a highly redundant posterior leaflet to treat a restrictive defect in the native anterior mitral leaflet. Also, this version can be used to treat anterior mitral leaflet prolapse by creating a large zone of coaptation in the left atrium.

Figure 15:
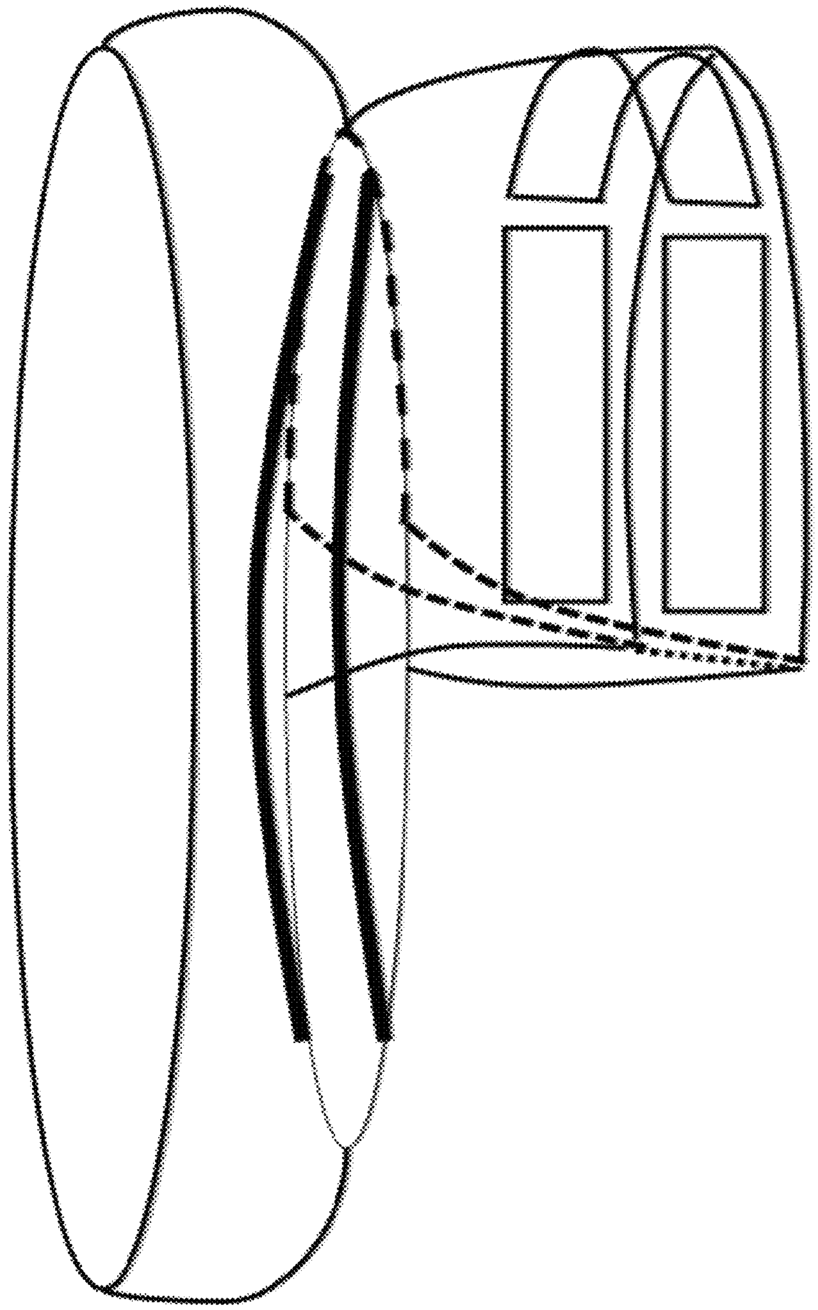
FIG. 15 illustrates an exemplary design of the valve prosthesis to include two structural barriers at or above the plane of the mitral annulus within the valvular prosthesis attached at two points along the inner circumference of the valvular device to prevent prolapse of the native anterior mitral leaflet during systole as that structure coapts against the prosthetic posterior mitral leaflet or leaflets.

Another embodiment of the device can include one or more inflatable chambers (see adjacent rectangular chambers in lower portion of prosthesis in FIG. 15) located within the circumference of the device below the tubular element of the device between the ventricular skirt of the device and the one or more prosthetic posterior leaflet equivalents. These inflatable chambers can be filled with liquid or gas or semisolid material at the time of implantation or remotely or through directly connected tubes to advance or retract the prosthetic posterior leaflet. This permits improvement of coaptation between the native anterior mitral leaflet and the prosthetic posterior leaflet(s).

Guided Valve Fixation

In order to steer the valve device and to fix the device in position, one exemplary embodiment can include techniques such as those described in the PCT application incorporated by reference herein, which in some embodiments provides two or more suture guides affixed to the outer circumference of the tubular element of the device to allow for directed placement and/or proper positioning of the device, orientation and fixation, such as illustrated in FIGS. 4A-E. These guides can be located, for example on the external circumference of the tubular element of the device. These suture guides can also be formed as holes or openings defined in the prosthesis frame or body, external rings, tubes or similar shapes. In one embodiment, two guides can be positioned anteriorly to approximate the distance between the right and left fibrous trigones. In another embodiment, the suture guides can be movable to dynamically fit the delivery and seating of the device to different anatomical sizes of mitral annulae. In another embodiment, the device can include one or more such guides on the posterior external circumference of the device with or without such guides on the anterior aspect of the device. These too can be fixed in position or be adjustable to approximate the distance between sutures placed in the native mitral annulus by a variety of techniques and imaged by a variety of techniques.

These guides can, if desired, be used in conjunction with a single suture, a loop of suture, and/or a rail of any material that could be fixed at an annular or periannular location to guide the device into location and possibly to fix the device in place. The suture guides can be used to drive the device into position in a beating heart. Once the device is delivered through the annulus, the ventricular portion of the device can be deployed to bring the ventricular skirt into coaptation with the endocardium of the left ventricle. This action can also incompletely deploy the atrial skirt of the device such that blood can immediately flow through the open central portion of the device, but without the user ever losing control of or being able to fully retrieve the device. The device can then be rotated to identify the best position of the prosthetic posterior mitral leaflet using a dynamic imaging study such as three-dimensional or two-dimensional echocardiography. The sutures or rails passed through the guides can then be tied and/or crimped and subsequently cut to fix the device in permanent position following full deployment.

Anterior Leaflet Prolapse Prevention Element

Figure 16:
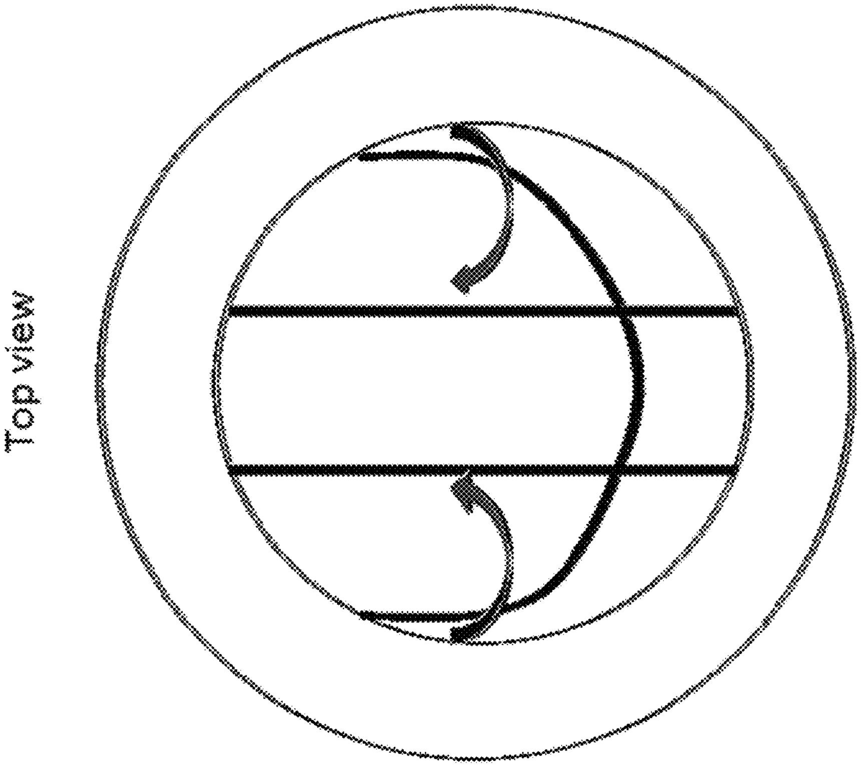
FIG. 16 illustrates a top-down view of an exemplary design of the valve prosthesis including an exemplary set of structural barriers to prevent anterior leaflet prolapse during systole. The two arrows represent how the structural barriers would move into position as the valve prosthesis was deployed from a catheter or other delivery device.
Figure 17:
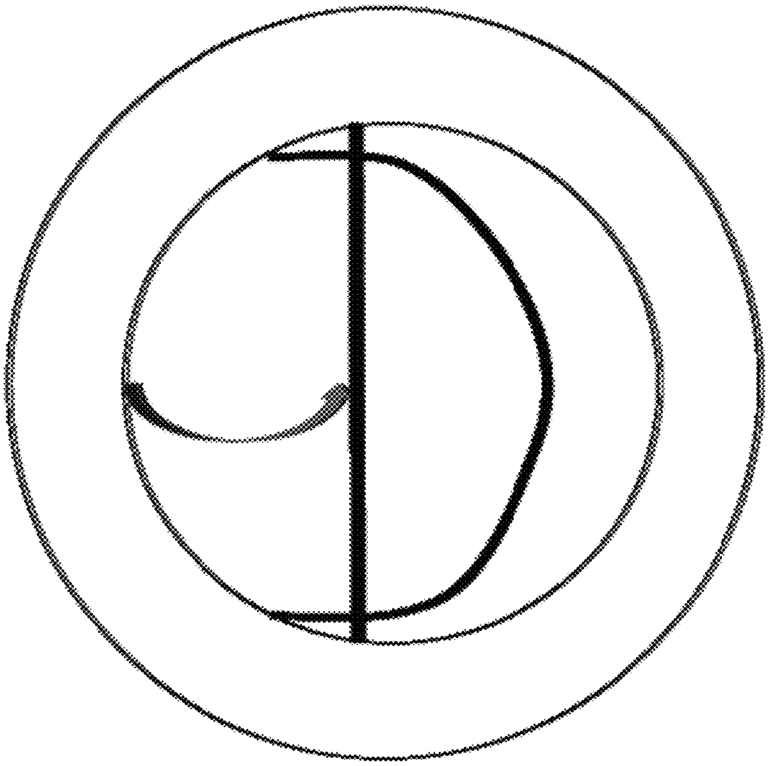
FIG. 17 illustrates an exemplary design of a single structural barrier to prevent anterior mitral leaflet prolapse during systole fixed transversely in the valve device. The arrow represents how the structural barriers would move into position as the valve prosthesis was deployed from a catheter or other delivery device.

Prolapse of the anterior leaflet of the mitral valve above the plane of the mitral annulus can result in mitral regurgitation as it fails to achieve coaptation with the posterior mitral leaflet. In some embodiments of the valve device, the device can include anterior-posterior and/or septal-lateral transversely directed "bars" or cords of biological or tissue compatible material such as PTFE or covered tantalum (e.g., see FIGS. 16-17) that spring into place upon deployment of the device at or above the annular plane to prevent anterior leaflet prolapse. These may also be flat straps of tissue compatible material or biological tissue that can rotate at their ends. These straps can rotate parallel to the direction of flow during diastole to avoid obstructing blood flow and then rotate flat during systole to increase the area of coverage of the potentially prolapsing anterior mitral leaflet.

Implantation Method

The valve device(s) described herein may be implanted surgically (on or off cardiopulmonary bypass) or as a minimally invasive surgical procedure. The device can also be implanted in one exemplary design as a fully catheter mounted device. As a fully catheter mounted device, the access to the mitral annulus can be, for example, through the left ventricular apex, through the free wall of the left atrium or through the left atrial septum.

The implant method for such device(s) can allow for rotation under imaging to properly position the partially deployed device and prosthetic posterior leaflet equivalent in conjunction with transesophageal (2D or 3D) or fluoroscopically.

In one embodiment, the external circumference of the annular level of the device can be coated with a fixed or expandable coating or element that can serve to prevent periprosthetic leak by occupying space between the external annular level of the device and the native mitral annulus. The annulus can be rendered irregularly shaped and firm by virtue of calcification. This element of the prosthesis can occupy such spaces between the irregularly shaped native mitral annulus and the uniformly circumferential external wall of the device.

Thus, in some embodiments the disclosure provides heart valve prosthesis that includes a tubular or “D”-shaped member configured for deployment in a heart valve annulus, first set of fastening mechanisms radially and outwardly disposed from the tubular or “D”-shaped member and configured to attach the valve prosthesis to cardiac tissue above the heart valve annulus, a second set of fastening mechanisms radially and outwardly disposed from the tubular or “D”-shaped member for less than the entire circumference of the tubular or “D”-shaped member and configured to attach the valve prosthesis to cardiac tissue below the heart valve annulus, and an incomplete covering/closure of the interior of the tubular or “D”-shaped member attached by any of various connectors to the inner circumference of the radially and outwardly disposed fastening mechanisms above, at or below the heart valve annulus. The first set of fastening mechanisms radially and outwardly disposed from the tubular or “D”-shaped member can be configured to attach the valve prosthesis to cardiac tissue above the heart valve annulus and can be interrupted for a section of the circumference where hooks, tines (and other connectors) can be disposed to attach the tubular or “D”-shaped member above the heart valve annulus. In some embodiments, two hooks can extend radially outward from the exterior of the tubular of “D”-shaped member for attachment to the myocardium below the annulus to secure the tubular of “D”-shaped member above the annulus. The incomplete covering/closure of the interior of the tubular or “D”-shaped member can be a unitary panel or can be interrupted in one or more sections with attachments to the second set of fastening mechanisms radially and outwardly disposed from the tubular or “D”-shaped member to prevent displacement of the incomplete covering or closure above the highest point of the tubular or “D”-shaped member above the annulus. The incomplete covering/closure of the interior of the tubular or “D”-shaped member may be composed of biological tissue. If desired, the device can be completely or partially constructed of biological material. The incomplete covering/closure of the interior of the tubular or “D”-shaped member may be fixed or mobile. The position of the incomplete covering/closure of the interior of the tubular or “D”-shaped member can be variably controlled by sutures or one or more remotely inflatable chambers. In some implementations, two or more rings can be laterally disposed from the external circumference of the tubular or “D”-shaped member. The rings can freely move in the plane along the external circumference of the tubular or “D”-shaped member until the device is fully deployed. One or more fixed or mobile bars or straps of tissue compatible material may cross the internal area of the tubular or “D”-shaped member or the first set of fastening mechanisms radially and outwardly disposed from the tubular or “D”-shaped member. The external circumference of the tubular or “D”-shaped member can include an expandable material or covering and/or remotely inflatable chambers to adhere to an irregularly shaped valve annulus and can either automatically or controllably oppose and seal the space between the annulus and the device. The device can contain a remote monitor to measure blood flow, blood pressure, heart rate or heart rhythm and transmit the data to a user terminal that can be viewed by a surgeon, physician or operating room assistant.

All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The methods and systems of the present disclosure, as described above and shown in the drawings, provide for improved techniques for treating mitral valves of patients. It will be apparent to those skilled in the art that various modifications and variations can be made in the devices, methods and systems of the present disclosure without departing from the spirit or scope of the disclosure. Thus, it is intended that the present disclosure include modifications and variations that are within the scope of the subject disclosure and equivalents.

What is claimed is:

1. A mitral valve prosthesis having an tubular upper portion to reside in an atrium and an downwardly depending posterior skirt to reside in the left ventricle, comprising:
- a tubular upper portion to reside in and urge against the walls of a patient’s atrium above and radially outwardly from the patient’s mitral annulus;
- a downwardly depending posterior skirt coupled to the tubular upper portion configured to be disposed in a delivery catheter, wherein the downwardly depending posterior skirt is configured to not extend below the mitral annulus in the region of an anterior native mitral valve leaflet of the patient after being deployed;
- wherein the mitral valve prosthesis is configured to be delivered into a patient’s heart using a delivery catheter;
- wherein the tubular upper portion of the mitral valve prosthesis is configured to be deployed from the delivery catheter within the patient’s left atrium, the tubular upper portion has a funnel shaped circumferential wall, and the funnel shaped tubular upper portion is configured to cause the funnel shaped circumferential wall to urge against cardiac tissue of the left atrium when the funnel shaped circumferential wall is deployed within the patient’s left atrium; and
- wherein the downwardly depending posterior skirt of the mitral valve prosthesis is configured to be deployed through the mitral annulus into the left ventricle, the downwardly depending posterior skirt is configured to not interfere with the opening and closing of the native anterior mitral valve leaflet and the mitral valve prosthesis further includes at least one posterior leaflet coupled to the downwardly depending posterior skirt that coapts with a native anterior mitral valve leaflet to permit the mitral valve to open and close.

2. The mitral valve prosthesis of claim 1, wherein the downwardly depending posterior skirt is configured to urge against an inner surface of the left ventricle to prevent flow around an outer portion of the valve prosthesis.

3. The mitral valve prosthesis of claim 1, wherein the mitral valve prosthesis further includes at least one lower fastener disposed proximate the downwardly depending posterior skirt that is configured to be deployed to hold the mitral valve prosthesis in place.

4. The mitral valve prosthesis of claim 3, wherein the at least one lower fastener includes a plurality of fasteners formed into the downwardly depending posterior skirt.

5. The mitral valve prosthesis of claim 4, wherein the at least one lower fastener includes at least one fastener disposed radially outwardly from the downwardly depending posterior skirt that urges upwardly against the ventricular side of the mitral annulus.

6. The mitral valve prosthesis of claim 1, further comprising at least one inflatable bladder coupled to the prosthesis configured to be inflated outwardly against a surface of the left ventricle to prevent flow around an outside of the prosthesis.

7. The mitral valve prosthesis of claim 6, wherein the at least one inflatable bladder is disposed along a portion of the downwardly depending posterior skirt.

8. The mitral valve prosthesis of claim 6, wherein the at least one inflatable bladder includes a plurality of adjacent chambers.

9. The mitral valve prosthesis of claim 8, wherein the plurality of adjacent chambers are arranged circumferentially about the downwardly depending posterior skirt.

10. The mitral valve prosthesis of claim 8, wherein each chamber in the plurality of adjacent chambers can be inflated individually.

11. The mitral valve prosthesis of claim 1, wherein the downwardly depending posterior skirt is configured to be fastened against a posterior wall of the patient's left ventricle.

12. The mitral valve prosthesis of claim 1, wherein the funnel shaped tubular upper portion includes a plurality of distributed fasteners that are configured to urge against the walls of the left atrium to help to maintain the position of the mitral valve prosthesis within the mitral annulus.

13. The mitral valve prosthesis of claim 12, wherein the plurality of distributed fasteners at least partially define the shape of the funnel shaped tubular upper portion.

14. The mitral valve prosthesis of claim 1, wherein the mitral valve prosthesis is configured to exert a radially-outward force onto the left atrial endocardium, mitral annulus and left ventricular endocardium after the mitral valve prosthesis is deployed.

15. The mitral valve prosthesis of claim 1, further wherein the mitral valve prosthesis is configured to be fastened proximate the fibrous trigones of the mitral valve annulus.

16. The mitral valve prosthesis of claim 1, wherein the mitral valve prosthesis is configured to be rotated within the mitral annulus under imaging when the mitral valve prosthesis is in a partially deployed state to facilitate alignment of the mitral valve prosthesis with respect to native anatomy.

17. The mitral valve prosthesis of claim 1, wherein an external circumference of the mitral valve prosthesis is coated with a material to prevent a periprosthetic leak by occupying space between an external annular level of the device and the native mitral annulus.

18. The mitral valve prosthesis of claim 1, further comprising at least one guiding conduit to guide the mitral valve prosthesis to the mitral annulus over a guide rail.

19. The mitral valve prosthesis of claim 1, wherein the mitral valve prosthesis is configured to permit deployment of the downwardly depending posterior skirt to bring the downwardly depending posterior skirt into coaptation with the endocardium of the left ventricle while the tubular upper portion is incompletely deployed to permit blood to immediately flow through an open central portion of the mitral valve prosthesis.

20. The mitral valve prosthesis of claim 1, wherein the mitral valve prosthesis is configured to be fully retrieved before after it has been partially deployed in a left atrium and a left ventricle of a patient.

21. The mitral valve prosthesis of claim 1, wherein the tubular upper portion is funnel-shaped.

* * * * *